(12) United States Patent
Wood et al.

(10) Patent No.: US 8,507,477 B2
(45) Date of Patent: Aug. 13, 2013

(54) 3- AND 6-QUINOLINES WITH N-ATTACHED HETEROCYCLIC CGRP RECEPTOR ANTAGONISTS

(75) Inventors: Michael R. Wood, Brentwood, TN (US); Ian M. Bell, Harleysville, PA (US); June J. Kim, Collegeville, PA (US); Harold G. Selnick, Ambler, PA (US); Craig A. Stump, Pottstown, PA (US)

(73) Assignee: Merck, Sharp & Dohme, Corp., Rahway, NJ (US)

( * ) Notice: Subject to any disclaimer, the term of this patent is extended or adjusted under 35 U.S.C. 154(b) by 74 days.

(21) Appl. No.: 13/059,164

(22) PCT Filed: Aug. 14, 2009

(86) PCT No.: PCT/US2009/053804
§ 371 (c)(1),
(2), (4) Date: May 25, 2011

(87) PCT Pub. No.: WO2010/021919
PCT Pub. Date: Feb. 25, 2010

(65) Prior Publication Data
US 2011/0306604 A1    Dec. 15, 2011

Related U.S. Application Data

(60) Provisional application No. 61/189,298, filed on Aug. 18, 2008.

(51) Int. Cl.
*C07D 487/10* (2006.01)
*A61K 31/55* (2006.01)
*A61P 25/06* (2006.01)

(52) U.S. Cl.
USPC ........... 514/221; 514/249; 514/278; 514/280; 540/500; 544/231; 544/361; 546/16; 546/18; 546/48

(58) Field of Classification Search
USPC ................ 514/221, 249, 278, 280; 540/500; 544/231, 361; 546/16, 18, 48
See application file for complete search history.

(56) References Cited

U.S. PATENT DOCUMENTS

| | | | |
|---|---|---|---|
| 7,390,798 B2 | 6/2008 | Williams et al. | |
| 7,851,464 B2 | 12/2010 | Bell et al. | |
| 2009/0239870 A1 | 9/2009 | Bell et al. | |

FOREIGN PATENT DOCUMENTS

| | | | |
|---|---|---|---|
| WO | 2007061676 A2 | | 5/2007 |
| WO | 2007061677 A2 | | 5/2007 |
| WO | 2007061696 A2 | | 5/2007 |
| WO | WO 2007061694 | * | 5/2007 |
| WO | 2008073251 A1 | | 6/2008 |

* cited by examiner

*Primary Examiner* — Bruck Kifle
(74) *Attorney, Agent, or Firm* — Nicole M. Beeler; Gerard M. Devlin

(57) ABSTRACT

Compounds of Formula (I): (where variables $R^{1A}$, $R^{1B}$, $R^2$, $R^3$, $R^4$, A, and Z are as defined herein) which are useful as antagonists of CGRP receptors, and useful in the treatment or prevention of diseases in which CGRP receptors are involved, such as headache, and in particular migraine and cluster headache. The invention is also directed to pharmaceutical compositions comprising these compounds and the use of these compounds and compositions in the prevention or treatment of such diseases in which CGRP receptors are involved.

(I)

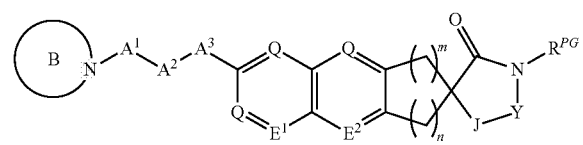

21 Claims, No Drawings

3- AND 6-QUINOLINES WITH N-ATTACHED HETEROCYCLIC CGRP RECEPTOR ANTAGONISTS

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human α-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of $CGRP_2$. CGRP is a potent neuromodulator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187), salivary levels of CGRP are elevated in migraine subjects between attacks (Bellamy et al., Headache, 2006, 46, 24-33), and CGRP itself has been shown to trigger migrainous headache (Lassen et al., Cephalalgia, 2002, 22, 54-61). In clinical trials, the CGRP antagonist BIBN4096BS has been shown to be effective in treating acute attacks of migraine (Olesen et al., New Engl. J. Med., 2004, 350, 1104-1110) and was able to prevent headache induced by CGRP infusion in a control group (Petersen et al., Clin. Pharmacol. Ther., 2005, 77, 202-213).

CGRP-mediated activation of the trigeminovascular system may play a key role in migraine pathogenesis. Additionally, CGRP activates receptors on the smooth muscle of intracranial vessels, leading to increased vasodilation, which is thought to contribute to headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99), Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP ), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358); morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache.

The present invention relates to compounds that are useful as ligands for CGRP receptors, in particular antagonists for CGRP receptors, processes for their preparation, their use in therapy, pharmaceutical compositions comprising them and methods of therapy using them.

The present invention is directed to compounds of the formula I:

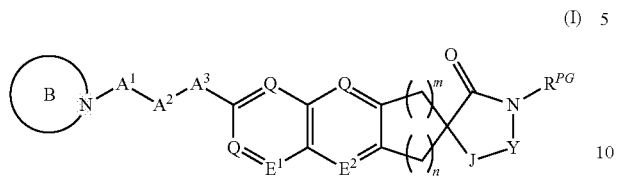

(wherein variables $A^1$, $A^2$, $A^3$, ring-B, m, n, J, Q, $E^1$, $E^2$, $R^{PG}$ and Y are as described herein) which are antagonists of CGRP receptors and which are useful in the treatment or prevention of diseases in which the CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of the formula I:

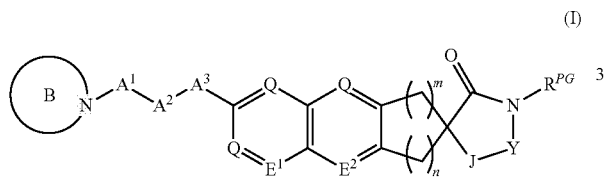

wherein:
$E^1$ and $E^2$ are selected from:
  (1) =N—,
  (2) =$N^+(O^-)$—, and
  (3) =$C(R^5)$—;
wherein at least one of $E^1$ and $E^2$ must contain nitrogen;
Q is selected from:
  (1) =N—,
  (2) =$N^+(O^-)$—, and
  (3) =$C(R^5)$—;
$A^1$, $A^2$ and $A^3$ are each independently selected from:
  (1) a bond,
  (2) —$CR^1R^2$—,
  (3) —$NR^b$—,
  (4) —$CR^1R^2$—$NR^b$—,
  (5) —$CR^1R^2$—$CH_2$—,
  (6) —O—$CR^1R^2$—,
  (7) —$CR^1R^2$—O—, and
  (8) —C(=O)—;
  provided that at least one of $A^1$, $A^2$ and $A^3$ is not a bond;
$R^1$ and $R^2$ are each independently selected from:
  (1) hydrogen,
  (2) $C_{1-6}$ alkyl, which is unsubstituted or substituted with 1-5 substituents each independently selected from:
    (a) —$C_{3-6}$cycloalkyl, which is unsubstituted or substituted with 1-5 halo,
    (b) —$OR^a$,
    (c) halo, and
    (d) phenyl, which is unsubstituted or substituted with 1-5 halo,
  (3) —$OR^a$,
  (4) halo, and
  (5) phenyl or pyridinyl, which is unsubstituted or substituted with 1-5 substituents each independently selected from:
    (a) halo,
    (b) —$OR^a$,
    (c) —CN, and
    (d) —$C_{1-6}$alkyl, which is unsubstituted or substituted with 1-5 halo;
$R^5$ is independently selected from:
  (1) hydrogen
  (2) —$C_{1-6}$alkyl, which is unsubstituted or substituted with 1-6 halo,
  (3) halo,
  (4) —$OR^a$, and
  (5) —CN;
B is a heterocycle selected from the group consisting of:

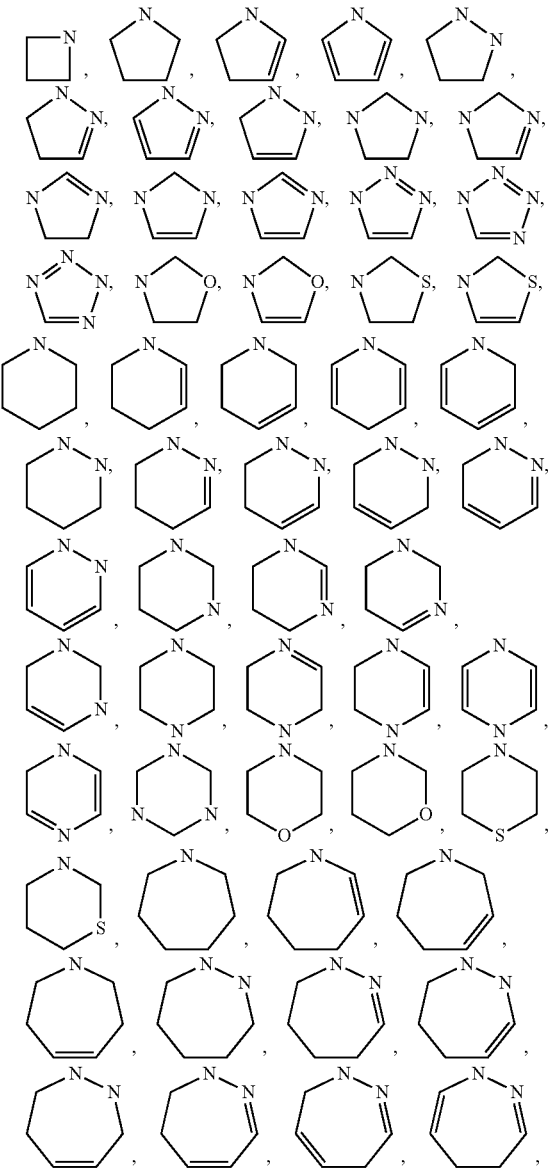

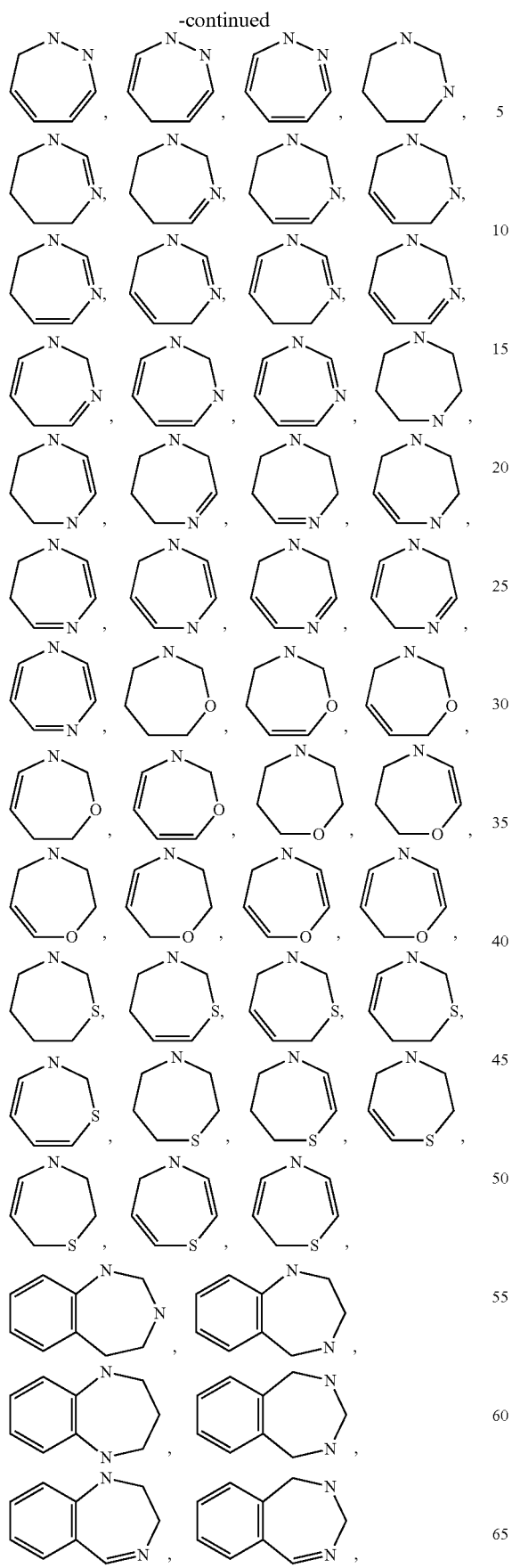
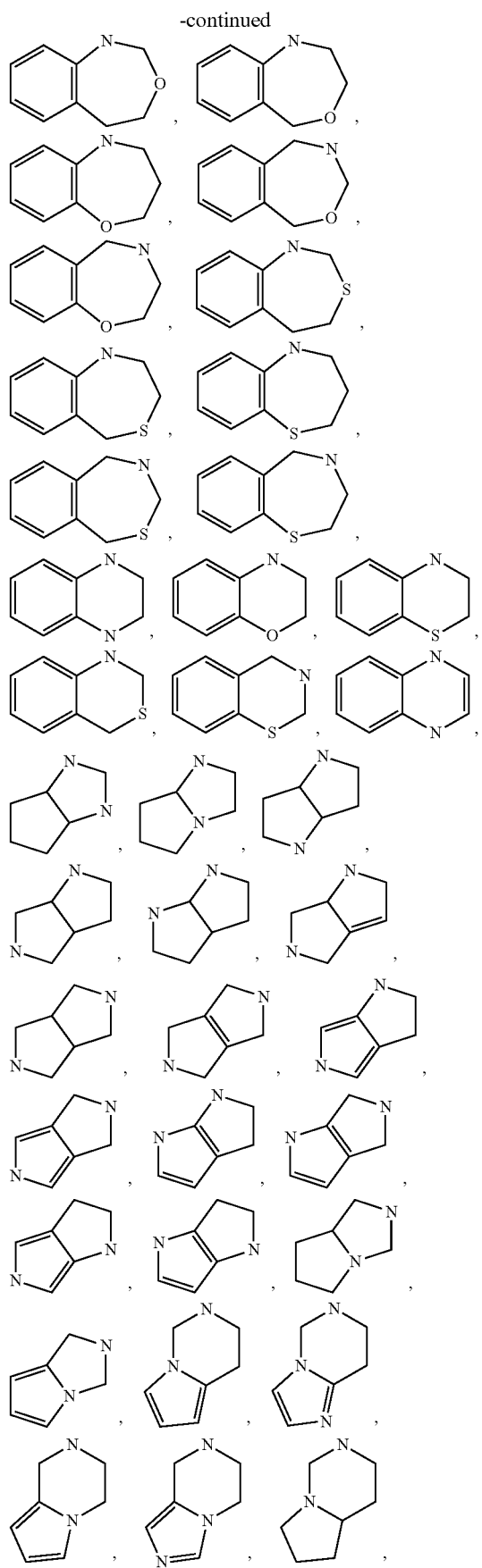

-continued

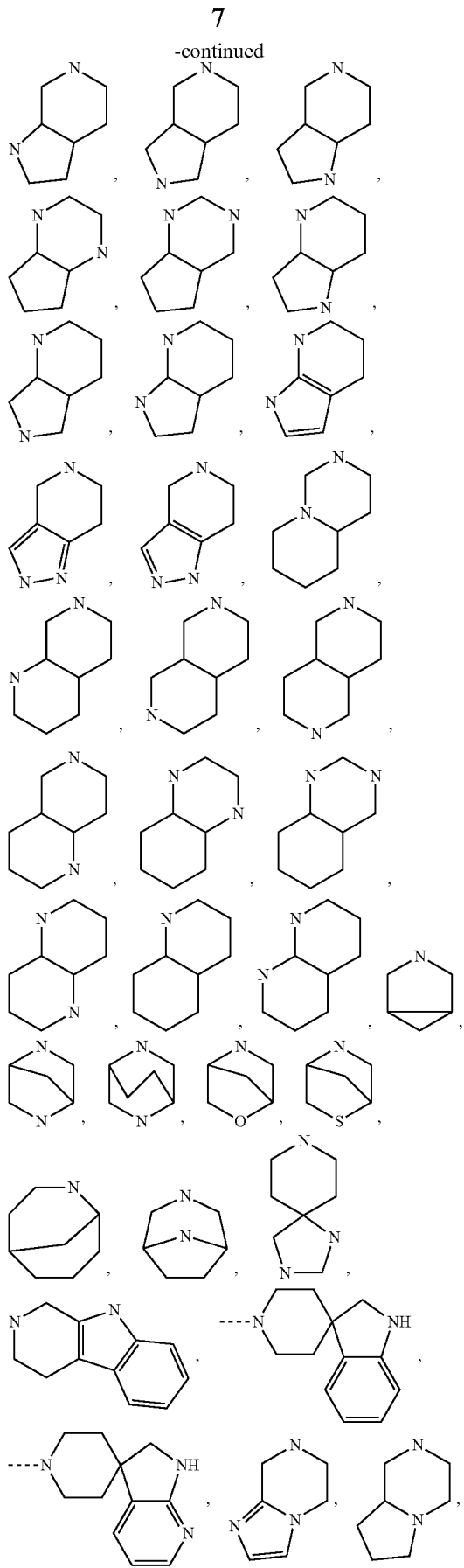

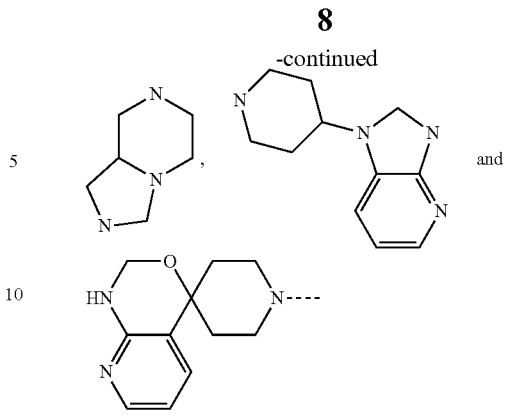

where B is linked to A¹ via a nitrogen atom in B and
where B is unsubstituted or substituted with 1-6 substitutents independently selected from $R^3$, $R^4$, $R^6$, $R^7$, $R^8$ and $R^9$;

$R^3$, $R^4$, $R^6$, $R^7$, $R^8$ and $R^9$ are each independently selected from:
(1) hydrogen,
(2) —$C_{1-6}$alkyl, which is unsubstituted or substituted with 1-5 substituents each independently selected from:
    (a) halo,
    (b) —$OR^a$,
    (c) —$C_{3-6}$cycloalkyl,
    (d) phenyl or heterocycle, wherein said heterocycle is selected from: benzodioxolyl, imidazolyl, indolyl, pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from
        (1) halo,
        (ii) —$C_{1-6}$alkyl, which is unsubstituted or substituted with 1-5 halo, and
        (iii) —$OR^a$,
    (e) —$CO_2R^a$,
    (f) —$C(=O)NR^bR^c$,
    (g) —$S(O)_vR^d$,
    (h) —CN,
    (i) —$NR^bR^c$,
    (j) —$N(R^b)C(=O)R^a$,
    (k) —$N(R^b)SO_2R^d$,
    (l) —$CF_3$,
    (m) —$O$—$CO_2R^d$,
    (n) —$O$—$(C=O)$—$NR^bR^c$,
    (o) —$NR^b$—$(C=O)$—$NR^bR^c$, and
    (p) —$C(=O)R^a$,
(3) —$C_{3-6}$cycloalkyl, which is unsubstituted or substituted with 1-5 substituents each independently selected from:
    (a) halo,
    (b) —CN,
    (c) —$C_{1-6}$alkyl, which is unsubstituted or substituted with 1-5 halo,
    (d) —$OR^a$, and
    (e) phenyl, which is unsubstituted or substituted with 1-5 substituents each independently selected from:
        (i) —$OR^a$,
        (ii) halo,
        (iii) —CN, and
        (iv) —$C_{1-6}$alkyl, which is unsubstituted or substituted with 1-5 halo,
(4) phenyl or heterocycle, wherein said heterocycle is selected from: benzimidazolyl, benzoxazinyl, benzoxazolyl, indanyl, indolyl, morpholinyl, oxadiazolyl, oxazolyl, pyridyl, pyrimidinyl, pyrazinyl, pyrazolyl, pyridazinyl, piperidinyl, piperazinyl, pyrrolidinyl, thienyl, tetrazolyl, thiazolyl, and triazolyl, which phenyl or heterocycle is unsubstituted or substituted with 1-5 substituents each independently selected from:
  (a) halo,
  (b) —$OR^a$,
  (c) —$C_{3-6}$cycloalkyl,
  (d) phenyl or pyridyl, which is unsubstituted or substituted with 1-5 substituents each independently selected from:
    (i) halo,
    (ii) $C_{1-6}$alkyl, which is unsubstituted or substituted with 1-6 halo, and
    (iii) —$OR^a$,
  (e) —$CO_2R^a$,
  (f) —$C(=O)NR^bR^c$,
  (g) —$S(O)_vR^d$,
  (h) —CN,
  (i) —$NR^bR^c$,
  (j) —$N(R^b)C(=O)R^a$,
  (k) —$N(R^b)SO_2R^d$,
  (l) —O—$CO_2R^d$,
  (m) —O—(C=O)—$NR^bR^c$,
  (n) —$NR^b$—(C=O)—$NR^bR^c$,
  (o) oxo,
  (p) —$C(=O)R^a$, and
  (q) —$C_{1-6}$alkyl, which is unsubstituted or substituted with 1-6 halo,
(5) halo,
(6) oxo,
(7) —$OR^a$,
(8) —CN,
(9) —$CO_2R^a$,
(10) —$C(=O)R^a$,
(11) —$NR^bR^c$,
(12) —$S(O)_vR^d$,
(13) —$C(=O)NR^bR^c$,
(14) —O—$(C=O)R^a$,
(15) —O—$CO_2R^d$,
(16) —$N(R^b)CO_2R^d$,
(17) —O—(C=O)—$NR^bR^c$,
(18) —$NR^b$—(C=O)—$NR^bR^c$,
(19) —$SO_2NR^bR^c$, and
(20) —$N(R^b)SO_2R^d$,
or $R^7$ and $R^8$ and the atom(s) to which they are attached join to form a ring selected from azetidinyl, aziridinyl, cyclobutyl, cycloheptyl, cyclohexyl, cyclooctyl, cyclopentyl, cyclopropyl, dihydrobenzofuranyl, dihydrobenzopyranyl, dioxanyl, dioxoalanyl, indanyl, indenyl, indolinyl, isoindolinyl, morpholinyl, oxetanyl, piperazinyl, piperidinyl, pyrrolidinyl, tetrahydrofuranyl, tetrahydroisoquinolinyl, tetrahydronaphthyl, tetrahydroquinolinyl, tetrahydropyranyl, tetrahydrothiapyranyl, tetrahydrothienyl, thiamorpholinyl, and thietanyl, wherein the sulfur is optionally oxidized to the sulfone or sulfoxide, which ring is unsubstituted or substituted with 1-5 substituents each independently selected from:
  (a) —$C_{1-6}$alkyl, which is unsubstituted or substituted with 1-3 substituents each independently selected from:
    (i) halo,
    (ii) —$OR^a$,
    (iii) —$C_{3-6}$cycloalkyl,
    (iv) —$CO_2R^a$,
    (v) —$NR^bR^c$,
    (vi) —$S(O)_vR^d$,
    (vii) —$C(=O)NR^bR^c$, and
    (viii) phenyl, which is unsubstituted or substituted with 1-5 halo,
  (b) phenyl or heterocycle, wherein heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, wherein the phenyl or heterocycle is optionally fused to the ring, and which phenyl or heterocycle is unsubstituted or substituted with 1-5 substituents each independently selected from:
    (i) halo,
    (ii) —$C_{1-6}$alkyl, which is unsubstituted or substituted with 1-5 halo, and
    (iii) —$OR^a$,
  (c) —$OR^a$,
  (d) halo,
  (e) —$CO_2R^a$,
  (f) —$C(=O)NR^bR^c$,
  (g) —$S(O)_vR^d$,
  (h) —CN,
  (i) —$NR^bR^c$,
  (j) —$N(R^b)C(=O)R^a$,
  (k) —$N(R^b)SO_2R^d$,
  (l) —O—$(C=O)R^a$,
  (m) —O—$CO_2R^d$,
  (n) —O—(C=O)—$NR^bR^c$,
  (o) —$NR^b$—(C=O)—$NR^bR^c$,
  (p) —$C(=O)R^a$, and
  (q) oxo;
$R^{PG}$ is independently selected from:
  (1) hydrogen,
  (2) —$C_{1-6}$alkyl which is unsubstituted or substituted with 1-5 halo,
  (3) —$CH_2OR^a$,
  (4) —$CH_2$—O—$CH_2CH_2Si(CH_3)_3$,
  (5) —$(CH_2)_k$-phenyl, which is unsubstituted or substituted with 1-3 substituents each independently selected from:
    (a) halo,
    (b) —$OR^a$,
    (c) —CN, and
    (d) —$C_{1-6}$alkyl, which is unsubstituted or substituted with 1-6 halo;
J is independently selected from:
  (1) =$C(R^{16a})$—,
  (2) —$CR^{17}R^{18}$—,
  (3) —C(=O)—, and
  (4) —$N(R^b)$—;
Y is independently selected from:
  (1) =$C(R^{16b})$—,
  (2) —$CR^{17}R^{18}$—,
  (3) —C(=O)—,
  (4) =N—, and
  (5) —$N(R^{16b})$—;
$R^{17}$ and $R^{18}$ are each independently selected from:
  (1) hydrogen,
  (2) halo,
  (3) —$OR^a$,
  (4) —$C_{1-6}$alkyl, which is unsubstituted or substituted with 1-4 substituents each independently selected from:
    (a) halo,
    (b) —$OR^a$,
    (c) —CN,
    (d) phenyl or heterocycle, wherein said heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from:
  (i) —$OR^a$,
  (ii) halo,
  (iii) —CN,
  (iv) —$C_{1-6}$alkyl which is unsubstituted or substituted with 1-6 halo,
(5) phenyl or heterocycle wherein heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from:
  (a) halo,
  (b) —CN,
  (c) —$OR^a$,
  (d) nitro,
  (e) —$C_{1-6}$alkyl which is unsubstituted or substituted with 1-6 halo;
or $R^{17}$ and $R^{18}$ and the atom to which they are attached join to form a 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
  (a) halo,
  (b) —$OR^a$,
  (c) —$C_{1-6}$alkyl, which is unsubstituted or substituted with 1-6 halo, and
  (d) phenyl, which is unsubstituted or substituted with 1-6 halo;
$R^{16a}$ and $R^{16b}$ are each independently selected from:
(1) hydrogen,
(2) —$C_{1-4}$alkyl, which is unsubstituted or substituted with 1-5 substituents each independently selected from:
  (a) halo,
  (b) —$OR^a$,
  (c) —$C_{3-6}$cycloalkyl,
  (d) phenyl or heterocycle, wherein said heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl, isoxazolyl and morpholinyl, which phenyl or heterocycle is unsubstituted or substituted with 1-3 substituents each independently selected from:
    (i) halo,
    (ii) —$OR^a$,
    (iii) —CN, and
    (iv) —$C_{1-6}$alkyl, which is unsubstituted or substituted with 1-6 halo,
(3) phenyl or heterocycle, wherein heterocycle is selected from: imidazolyl, oxazolyl, pyridyl, pyrimidinyl, pyrazinyl, pyridazinyl, tetrahydrofuryl, piperidinyl, piperazinyl, pyrrolidinyl, azetidinyl, thiazolyl, thienyl, triazolyl, isoxazolyl and morpholinyl, which phenyl or heterocycle is unsubstituted or substituted with 1-3 substituents each independently selected from:
  (a) halo,
  (b) —$OR^a$,
  (c) —$C_{3-6}$cycloalkyl,
  (d) —$C_{1-4}$alkyl which is unsubstituted or substituted with 1-6 halo, and
  (e) phenyl, which is unsubstituted or substituted with 1-5 substituents each independently selected from:
    (i) halo,
    (ii) —$C_{1-6}$alkyl, which is unsubstituted or substituted with 1-6 halo, and
    (iii) —$OR^a$,
(4) halo,
(5) —$OR^a$,
(6) —CN,
(7) —$CO_2R^a$,
(8) —$NR^bR^c$, and
(9) —C(=O)$NR^bR^c$,
or $R^{16a}$ and $R^{16b}$ and the atom(s) to which they are attached join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:
  (a) —$C_{1-6}$alkyl, which is unsubstituted or substituted with 1-3 substituents each independently selected from:
    (i) halo,
    (ii) —$OR^a$,
    (iii) —$C_{3-6}$cycloalkyl,
    (iv) phenyl or heterocycle, wherein heterocycle is selected from pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from:
      (I) —$OR^a$,
      (II) halo,
      (III) —CN, and
      (IV) —$C_{1-6}$alkyl which is unsubstituted or substituted with 1-6 halo,
    (v) —$CO_2R^a$,
    (vi) —$NR^bR^c$,
    (vii) —$S(O)_vR^d$,
    (viii) —C(=O)$NR^bR^c$,
    (ix) —N($R^b$)$CO_2R^a$, and
    (x) —N($R^b$)$SO_2R^d$,
  (b) phenyl or heterocycle, wherein said heterocycle is selected from pyridyl, pyrimidinyl, pyrazinyl, pyridazinyl, piperidinyl, azetidinyl, piperazinyl, pyrrolidinyl, thienyl and morpholinyl, which phenyl or heterocycle is unsubstituted or substituted with 1-5 substituents each independently selected from:
    (i) halo,
    (ii) —$OR^a$,
    (iii) —CN, and
    (iv) —$C_{1-6}$alkyl which is unsubstituted or substituted with 1-6 halo,
  (c) halo,
  (d) —$S(O)_vR^d$,
  (e) —$OR^a$,
  (f) —CN,
  (g) —C(=O)$R^a$,
  (h) —$NR^bR^c$,
  (i) —C(=O)$NR^bR^c$,
  (j) —$CO_2R^a$,
  (k) —($NR^b$)$CO_2R^a$,
  (l) —O—(C=O)—$NR^bR^a$,
  (m) —($NR^b$)—(C=O)—$NR^bR^c$,
  (n) oxo, and
  (o) —($NR^b$)$SO_2R^d$;

$R^a$ is independently selected from:
(1) hydrogen,
(2) $C_{1-6}$alkyl, which is unsubstituted or substituted with 1-7 substituents each independently selected from:
  (a) halo,
  (b) —O—$C_{1-6}$alkyl, which is unsubstituted or substituted with 1-6 halo,
  (c) hydroxyl,
  (d) —C(=O)—O—$C_{1-6}$alkyl, which is unsubstituted or substituted with 1-6 halo,
  (e) —CN, and
  (f) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (i) halo,
    (ii) —O—$C_{1-6}$alkyl, which is unsubstituted or substituted with 1-6 halo,
    (iii) —CN,
    (iv) nitro,
    (v) hydroxyl, and
    (vi) —$C_{1-6}$alkyl, which is unsubstituted or substituted with 1-6 halo,
(3) phenyl or heterocycle wherein said heterocycle is selected from pyridyl, indolyl, pyrimidinyl, thienyl, pyridazinyl, piperidinyl, azetidinyl, furanyl, piperazinyl, pyrrolidinyl, morpholinyl, tetrahydropyranyl, tetrahydropyranyl and pyrazinyl, which phenyl or heterocycle is unsubstituted or substituted with 1-3 substituents each independently selected from:
  (a) halo,
  (b) —CN,
  (c) —O—$C_{1-6}$alkyl, which is unsubstituted or substituted with 1-6 halo,
  (d) nitro,
  (e) hydroxyl, and
  (f) —$C_{1-6}$alkyl, which is unsubstituted or substituted with 1-6 halo, and
(4) —$C_{3-6}$cycloalkyl, which is unsubstituted or substituted with 1-6 halo;
$R^b$ and $R^c$ are independently selected from:
(1) hydrogen,
(2) $C_{1-6}$alkyl, which is unsubstituted or substituted with 1-7 substituents each independently selected from:
  (a) halo,
  (b) —OR$^a$,
  (c) —CN,
  (d) —CO$_2$R$^a$,
  (e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (i) halo,
    (ii) —OR$^a$,
    (iii) —$C_{1-6}$alkyl, which is unsubstituted or substituted with 1-6 halo, and
    (iv) nitro,
  (3) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (a) halo,
    (b) —OR$^a$,
    (c) —$C_{1-6}$alkyl, which is unsubstituted or substituted with 1-6 halo,
    (d) —$C_{3-6}$cycloalkyl, which is unsubstituted or substituted with 1-6 halo,
    (e) —CN, and
    (f) —CO$_2$R$^a$,
(4) —$C_{3-6}$cycloalkyl, which is unsubstituted or substituted with 1-6 halo;
or $R^b$ and $R^c$ and the nitrogen to which they are attached join to form a 4-, 5-, or 6-membered ring optionally containing an additional heteroatom selected from N, O, and S, wherein the sulfur is optionally oxidized to the sulfone or sulfoxide, which ring is unsubstituted or substituted with 1-4 substituents each independently selected from:
  (a) halo,
  (b) —OR$^a$, and
  (c) —$C_{1-6}$alkyl, which is unsubstituted or substituted with 1-6 halo, and
  (d) phenyl;
$R^d$ is independently selected from:
(1) $C_{1-6}$alkyl, which is unsubstituted or substituted with 1-7 substituents each independently selected from:
  (a) halo,
  (b) —OR$^a$,
  (c) —CO$_2$R$^a$
  (d) —CN, and
  (e) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (i) halo,
    (ii) —OR$^a$,
    (iii) —CN,
    (iv) nitro, and
    (v) —$C_{1-6}$alkyl, which is unsubstituted or substituted with 1-6 halo,
(2) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
  (a) halo,
  (b) —OR$^a$,
  (c) —$C_{1-6}$alkyl, which is unsubstituted or substituted with 1-6 halo,
  (d) —$C_{3-6}$cycloalkyl, which is unsubstituted or substituted with 1-6 halo
  (e) nitro,
  (f) —CN, and
  (g) —CO$_2$R$^a$,
(3) —$C_{3-6}$cycloalkyl, which is unsubstituted or substituted with 1-6 halo;
m is 1, 2, or 3;
n is 1, 2, or 3;
v is 0, 1, or 2;
k is 0, 1, or 2;

and pharmaceutically acceptable salts thereof and tautomers thereof and individual enantiomers and diastereomers thereof.

In particular embodiments of the compounds of formula (I), each Q is =C(R$^5$)—. In these embodiments, typically each R$^5$ is hydrogen.

In particular embodiments of the compounds of formula (I), A$^2$ and A$^3$ are each a bond, and A$^1$ is selected form the group consisting of
(1) —CR$^1$R$^2$—,
(2) —NR$^b$—,
(3) —CR$^1$R$^2$—NR$^b$—,
(4) —CR$^1$R$^2$—CH$_2$—,
(5) —O—CR$^1$R$^2$—,
(6) —CR$^1$R$^2$—O—, and
(7) —C(=O)—.

In these embodiments, typically A$^1$ is —CR$^1$R$^2$—, and R$^1$ and R$^2$ are typically both hydrogen.

In particular embodiments of the compounds of formula (I), B is selected from the group consisting of

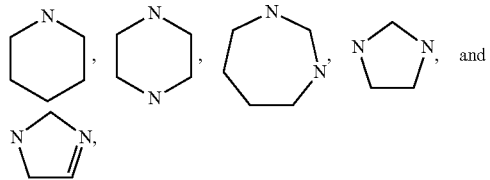

wherein B is unsubstituted or substituted with 1-6 substitutents independently selected from R$^3$, R$^4$, R$^6$, R$^7$, R$^8$ and R$^9$, and R$^3$, R$^4$, R$^6$, R$^7$, R$^8$ and R$^9$ are each independently selected from:
(1) hydrogen,
(2) —C$_{1-6}$alkyl, which is unsubstituted or substituted with 1-5 substituents each independently selected from:
  (a) halo,
  (b) —OR$^a$,
  (c) —C$_{3-6}$cycloalkyl,
  (d) phenyl, which phenyl is unsubstituted or substituted with 1-5 halogen,
(3) —C$_{3-6}$cycloalkyl, which is unsubstituted or substituted with 1-5 substituents each independently selected from:
  (a) halo,
  (b) CN,
  (c) —C$_{1-6}$alkyl, which is unsubstituted or substituted with 1-5 halo,
  (d) —OR$^a$, and
  (e) phenyl, which is unsubstituted or substituted with 1-5 substituents each independently selected from:
    (i) —OR$^a$,
    (ii) halo,
    (iii) —CN, and
    (iv) —C$_{1-6}$alkyl, which is unsubstituted or substituted with 1-5 halo,
(4) phenyl, which is unsubstituted or substituted with 1-5 halogen, and
(5) oxo,
or R$^7$ and R$^8$ and the atom(s) to which they are attached join to form a ring selected from cycloheptyl, cyclohexyl, cyclooctyl, cyclopentyl or tetrahydronaphthyl, which ring is unsubstituted or substituted with 1-5 substituents each independently selected from:

(a) —C$_{1-6}$alkyl, which is unsubstituted or substituted with 1-3 substituents each independently selected from halo,
(b) phenyl, wherein the phenyl is optionally fused to the ring, and which phenyl or heterocycle is unsubstituted or substituted with 1-5 substituents each independently selected from:
  (i) halo,
  (ii) —C$_{1-6}$alkyl, which is unsubstituted or substituted with 1-5 halo, and
  (iii) —OR$^a$.

In particular embodiments, B is selected from the group consisting of

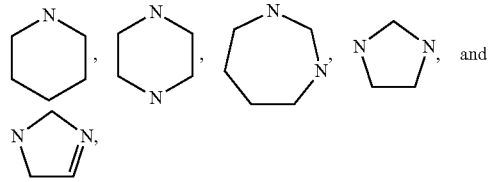

wherein B is unsubstituted or substituted with 1-6 substitutents independently selected from R$^3$, R$^4$, R$^6$, R$^7$, R$^8$ and R$^9$, and R$^7$ and R$^8$ and the atom(s) to which they are attached join to form a ring selected from cycloheptyl, cyclohexyl, cyclopentyl, and tetrahydronaphthyl.

In particular embodiments, B is selected from the group consisting of

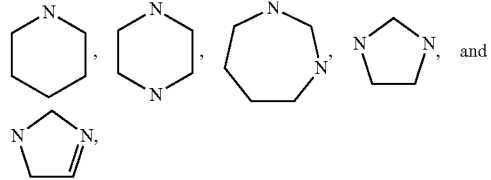

wherein B is substituted with 1-6 substitutents independently selected from R$^3$, R$^4$, R$^6$, R$^7$, R$^8$ and R$^9$, and at least one of R$^3$, R$^4$, R$^6$, R$^7$, R$^8$ and R$^9$ is oxo. In another embodiment, two of R$^3$, R$^4$, R$^6$, R$^7$, R$^8$ and R$^9$ are oxo.

In particular embodiments, B is selected from the group consisting of

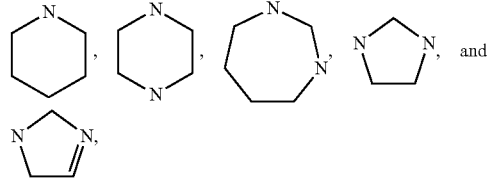

wherein B is unsubstituted or substituted with 1-6 substitutents independently selected from R$^3$, R$^4$, R$^6$, R$^7$, R$^8$ and R$^9$, and at least one of R$^3$, R$^4$, R$^6$, R$^7$, R$^8$ and R$^9$ is phenyl, optionally substituted with one or two halo (suitably, fluoro).

In particular embodiments of the compounds of formula (I), R$^{PG}$ is hydrogen.

In particular embodiments of the compounds of formula (I), m and n are each 1.

In particular embodiments of the compounds of formula (I), E$^1$ is nitrogen and E$^2$ is =C(R$^5$)—, wherein R$^5$ is suitably hydrogen. In other embodiments, $E^2$ is nitrogen and $E^1$ is $=C(R^5)$—, wherein $R^5$ is suitably hydrogen.

In particular embodiments of the compounds of formula (I), J is $=C(R^{16a})$— and Y is $=C(R^{16b})$—, and or $R^{16a}$ and $R^{16b}$ and the atom(s) to which they are attached join to form a ring selected from cyclopentenyl, cyclohexenyl, phenyl and pyridyl, wherein the ring is optionally substituted as described above. Typically, $R^{16a}$ and $R^{16b}$ are linked together to form an unsubstituted pyridyl ring.

In one embodiment of the invention, the compounds of formula (I) are compounds of formula (II)

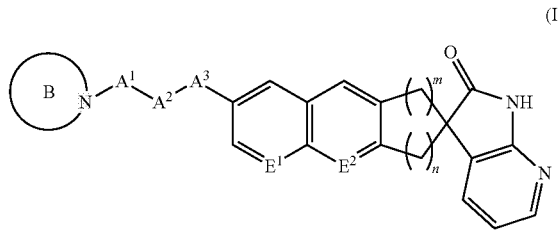

(II)

and pharmaceutically acceptable salts thereof and tautomers thereof and individual enantiomers and diastereomers thereof, wherein variables $A^1$, $A^2$, $A^3$, ring-B, m, n, $E^1$, $E^2$ and $R^{PG}$ are as described herein.

In one embodiment of the compounds of formula (II), $A^2$ and $A^3$ are each a bond, and $A^1$ is selected form the group consisting of (1) —$CR^1R^2$—,
(2) —$NR^b$—,
(3) —$CR^1R^2$—$NR^b$—,
(4) —$CR^1R^2$—$CH_2$—,
(5) —O—$CR^1R^2$—,
(6) —$CR^1R^2$—O—, and
(7) —C(=O)—.

Typically, in this embodiment, $A^1$ is —$CR^1R^2$—, and $R^1$ and $R^2$ are typically both hydrogen.

In particular embodiments of the compounds of formula (II), B is selected from the group consisting of

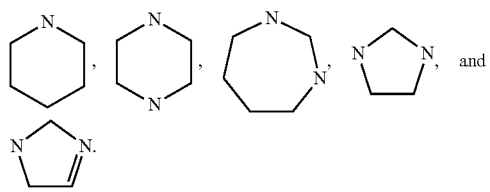

In particular embodiments of the compounds of formula (II), $R^{PG}$ is hydrogen.

In particular embodiments of the compounds of formula (II), m and n are each 1.

In particular embodiments of the compounds of formula (II), $E^1$ is nitrogen and $E^2$ is $=C(R^5)$—, wherein $R^5$ is suitably hydrogen. In other embodiments, $E^2$ is nitrogen and $E^1$ is $=C(R^5)$—, wherein $R^5$ is suitably hydrogen.

In one embodiment of the invention, the compounds of formula (I) are compounds of formula (III)

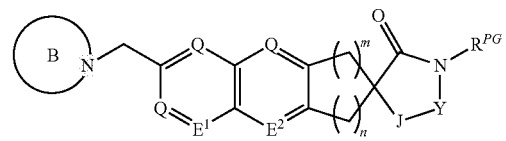

(III)

and pharmaceutically acceptable salts thereof and tautomers thereof and individual enantiomers and diastereomers thereof, wherein variables ring-B, m, n, Q, J, Y, $E^1$, $E^2$ and $R^{PG}$ are as described herein.

In particular embodiments of the compounds of formula (III), each Q is $=C(R)$—. Typically, each $R^5$ is hydrogen.

In particular embodiments of the compounds of formula (III), B is selected from the group consisting of

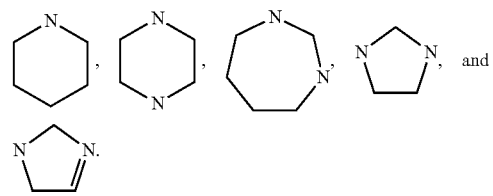

In particular embodiments of the compounds of formula (III), $R^{PG}$ is hydrogen.

In particular embodiments of the compounds of formula (III), m and n are each 1.

In particular embodiments of the compounds of formula (III), $E^1$ is nitrogen and $E^2$ is $=C(R^5)$—, wherein $R^5$ may be hydrogen. In other embodiments, $E^2$ is nitrogen and $E^1$ is $=C(R^5)$—, wherein $R^5$ is suitably hydrogen.

In particular embodiments of the compounds of formula (III), J is $=C(R^{16a})$— and Y is $=C(R^{16b})$—, and or $R^{16a}$ and $R^{16b}$ and the atom(s) to which they are attached join to form a ring selected from cyclopentenyl, cyclohexenyl, phenyl and pyridyl, wherein the ring is optionally substituted as described above. Typically, $R^{16a}$ and $R^{16b}$ are linked together to form an unsubstituted pyridyl ring.

In one embodiment of the invention, the compounds of formula (I) are compounds of formula (IV)

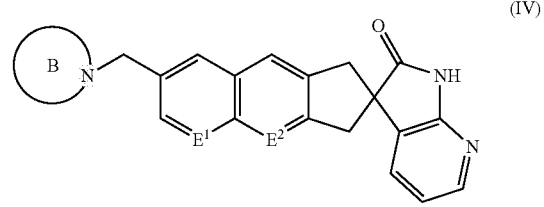

(IV)

and pharmaceutically acceptable salts thereof and tautomers thereof and individual enantiomers and diastereomers thereof, wherein variables ring-B, $E^1$ and $E^2$ are as described herein.

In particular embodiments of the compounds of formula (IV), B is selected from the group consisting of

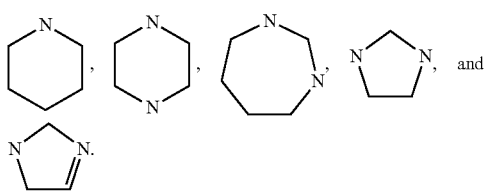

In particular embodiments of the compounds of formula (IV), $E^1$ is nitrogen and $E^2$ is =C($R^5$)—, wherein $R^5$ is suitably hydrogen. In other embodiments, $E^2$ is nitrogen and $E^1$ is =C($R^5$)—, wherein $R^5$ is suitably hydrogen.

The present invention is further directed to the exemplary compounds 1-21 of formula (I),
and pharmaceutically acceptable salts thereof.

The invention is also directed to medicaments or pharmaceutical compositions for treating diseases or disorders in which CGRP is involved, such as migraine, which comprise a compound of formula (I), or a pharmaceutically acceptable salt thereof, and a pharmaceutically acceptable carrier.

The invention is also directed to the use of a compound of formula (I) for treating diseases or disorders in which CGRP is involved, such as migraine.

The invention is further directed to a method for the manufacture of a medicament or a composition for treating diseases or disorders in which CGRP is involved, such as migraine, comprising combining a compound of formula (I) with one or more pharmaceutically acceptable carriers.

It is to be understood that where one or more of the above recited structures or substructures recite multiple substituents having the same designation each such variable may be the same or different from each similarly designated variable. For example, $R^a$ is recited multiple times in formula I, and each $R^a$ in formula I may independently be any of the substructures defined under $R^a$. The invention is not limited to structures and substructures wherein each $R^a$ must be the same for a given structure. The same is true with respect to any variable appearing multiple times in a structure or substructure.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The present invention includes compounds of formula I wherein on or more hydrogen atoms are replaced by deuterium.

Tautomers of compounds defined in Formula I are also included within the scope of the present invention. For example, compounds including carbonyl —$CH_2C(O)$— groups (keto forms) may undergo tautomerism to form hydroxyl —CH=C(OH)— groups (enol forms). Both keto and enol forms are included within the scope of the present invention.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to faint a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, even where substituents are disclosed which may form a ring structure (for instance $R^7$ may form a ring with $R^8$, $R^{16a}$ may form a ring with $R^{16b}$, etc.), not all combinations of substituents are susceptible to ring formation. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear or branched structures having no carbon-to-carbon double or triple bonds. Thus $C_{1-6}$alkyl is defined to identify the group as having 1, 2, 3, 4, 5 or 6 carbons in a linear or branched arrangement, such that $Cl_{1-6}$alkyl specifically includes, but is not limited to, methyl, ethyl, n-propyl, iso-propyl, n-butyl, iso-butyl, tert-butyl, pentyl and hexyl.

"Cycloalkyl" is an alkyl, part or all of which forms a ring of three or more atoms.

$C_0$ or $C_0$alkyl is defined to identify the presence of a direct covalent bond.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 5- to 7-membered monocyclic- or stable 8- to 11-membered bicyclic heterocyclic ring system which is either saturated or unsaturated, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxo-hexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$ alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, mane, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The number of certain variables present in certain instances is defined in terms of the number of carbons present. For example, variable "p" is occasionally defined as follows: "p is 0 to 2q+1, for a substituent with q carbons". Where the substituent is "$(F)_pC_{1-3}$ alkyl" this means that when there is one carbon, there are up to 2(1)+1=3 fluorines. When there are two carbons, there are up to 2(2)+1=5 fluorines, and when there are three carbons there are up to 2(3)+1=7 fluorines.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-migraine agent, such as ergotamine and dihydroergotamine, or other serotonin agonists, especially a $5\text{-HT}_{1B/1D}$ agonist, for example sumatriptan, naratriptan, zolmitriptan, eletriptan, almotriptan, frovatriptan, donitriptan, and rizatriptan, a $5\text{-HT}_{1D}$ agonist such as PNU-142633 and a $5\text{-HT}_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant; an NMDA antagonist; an NR2B antagonist; a bradykinin-1 receptor antagonist; an adenosine Al receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; a substance P antagonist; an endothelin antagonist; a norepinephrin precursor; anti-anxiety agents such as diazepam, alprazolam, chlordiazepoxide and chlorazepate; serotonin $5\text{HT}_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particularly preferred embodiment the present compounds are used in conjunction with an anti-migraine agent, such as: ergotamine or dihydroergotamine; a 5-$HT_1$ agonist, especially a 5-$HT_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

Reaction Schemes

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

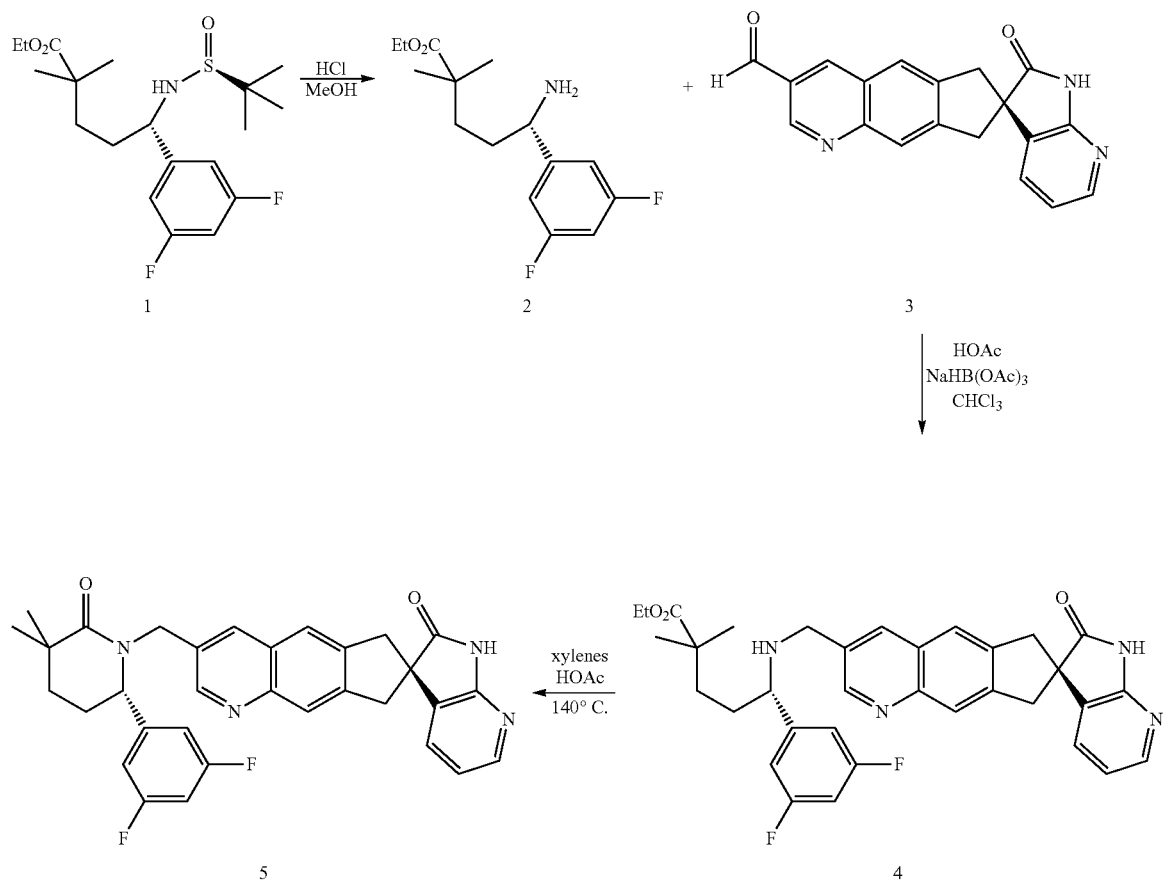

SCHEME 1

According to Scheme 1 sulfinamide 1 (U.S. Patent Application Publication No. US 2007/0265225) can be deprotected with the strong acid HCl, in MeOH, to provide, after basic aqueous work up, the amine 2. This amine can reductively alkylated with aldehyde 3 (Intermediate 1), in chloroform, using sodium triacetoxyborohydride and HOAc to yield secondary amine 4. Heating of this secondary amine to 140° C. in a 9/1 mixture of xylenes/HOAc results in lactamization to provide the claimed compound 5. A wide range of amino-esters can undergo the above procedure to provide a variety of claimed lactams.

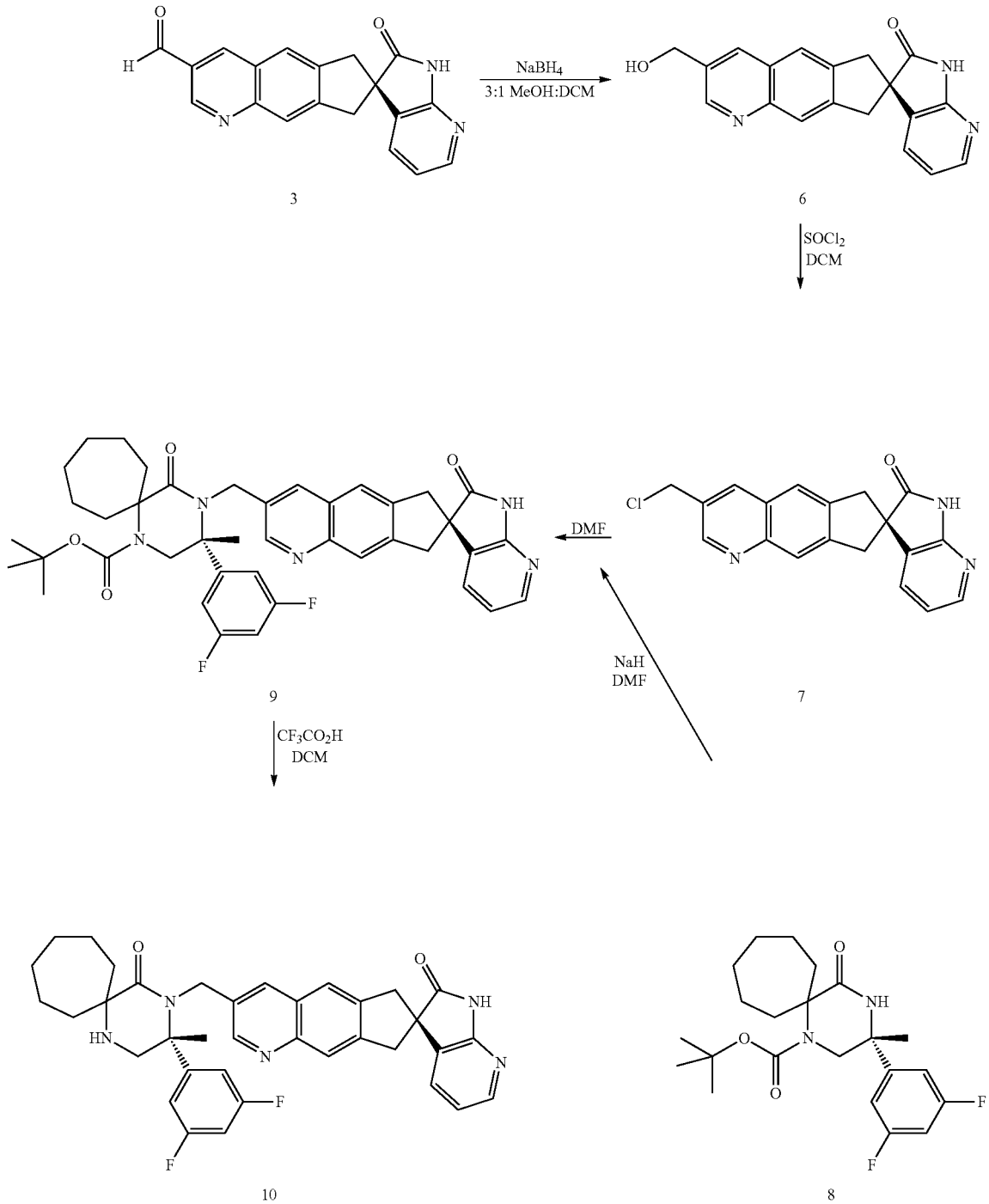

SCHEME 2

Aldehyde 3 can be reduced to alcohol 6, using sodium borohydride in a 3:1 mixture of MeOH/DCM at ambient temperature. This alcohol can then be converted to the chloride 7 using thionyl chloride in DCM. The electrophilic chloride 7 can then be used to alkylate a variety of nucleophiles. As shown in Scheme 2, one such nucleophile can be the sodium salt of compound 8 (Intermediate 10), prepared in DMF by its reaction with NaH, prior to the introduction of 7 to yield the claimed compound 9. The tert-butyl carbamate of this compound can be removed with trifluoroacetic acid in DCM, at ambient temperature, to provide the claimed compound 10. Examples of alternative heterocycles (but not limited to) which may be alkylated with 7 are shown in Schemes 3 and 4. Readily available ketones aldehydes may be converted to hydantoins under Bucherer-Bergs conditions, using ammonium carbonate and either sodium cyanide or potassium cyanide. Scheme 3 shows that the hydantoin 11, can be selectively alkylated at N-3 using potassium carbonate and 2-iodopropane, in DMF, to prepare 12 (Intermediate 3). Scheme 4 shows that the known amino amide 13 can be acylated with acid chloride 14, in DCM, using triethylamine as base, to provide 15. This primary amide can be cyclized, using aqueous sodium hydroxide, in MeOH, by heating to 90° C. to provide heterocycle 16.

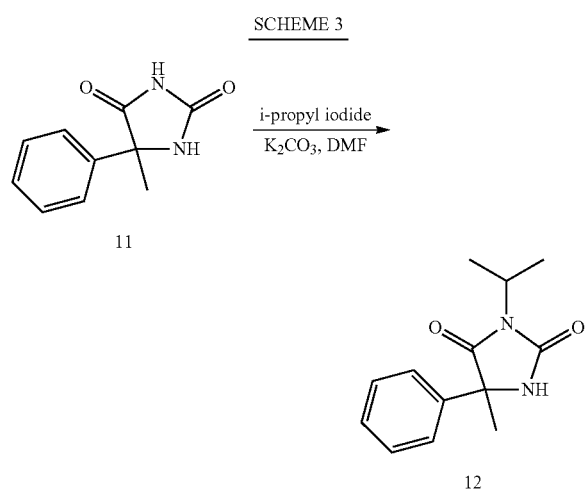

SCHEME 3

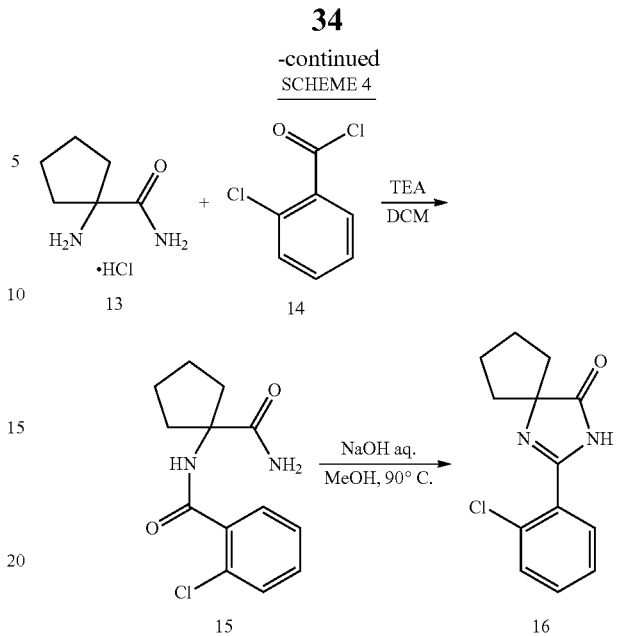

-continued
SCHEME 4

Scheme 5 shows the preparation of another CGRP antagonist starting from the known compound 17 (U.S. Patent Application Publication No. US 2007/0265225). This amine hydrochloride can be reductively alkylated on the less hindered, primary nitrogen using Hunig's base and sodium triacetoxyborohydride, in chloroform to give ester 18. The ester of 18 can be cleanly transformed into the potassium carboxylate 19 by the action of KOTMS (potassium trimethylsilanoate), in THF, at ~50° C. This potassium salt can then be cyclized using EDCI and HOAt, in DMF, to provide the claimed compound 20.

Additionally, some heterocycles may be directly alkylated, under reducing conditions to provide claimed compounds, as shown in Scheme 6. 2-Phenylpiperidine can react with aldehyde 3 (Intermediate 1), in chloroform, using sodium triacetoxyborohydride and HOAc to give the claimed compound 22.

SCHEME 5

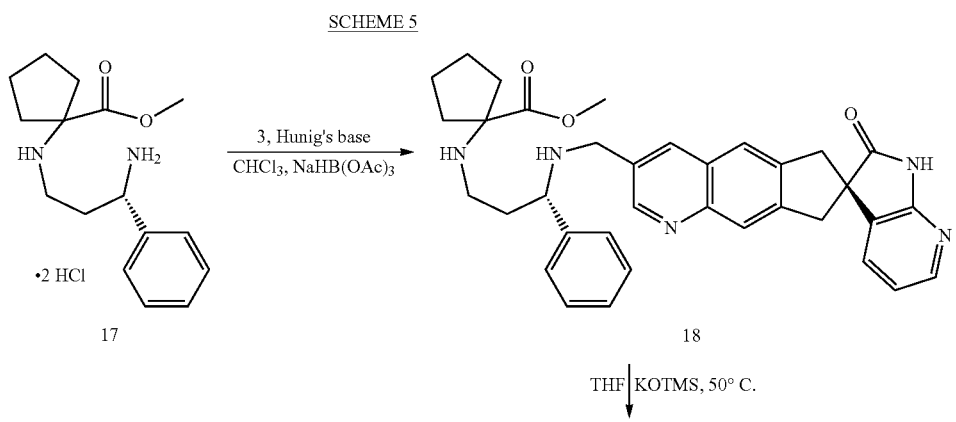

THF | KOTMS, 50° C.

35    36
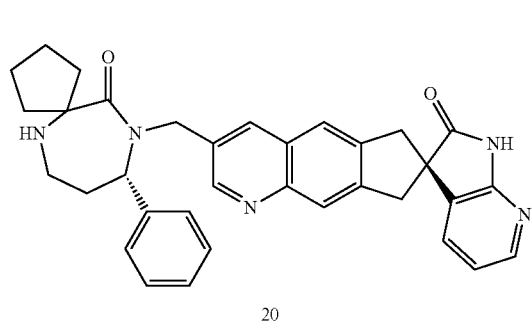
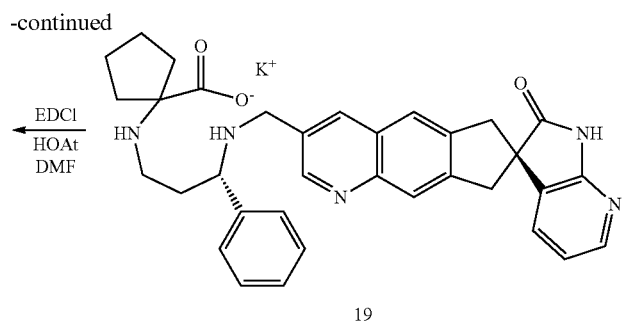
SCHEME 6
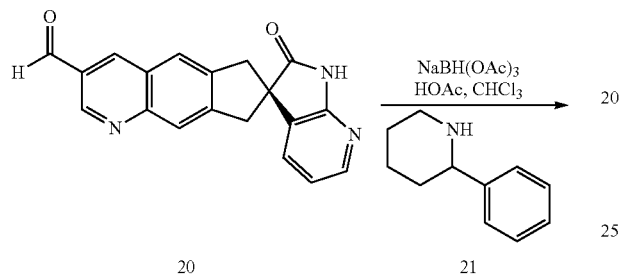
SCHEME 7
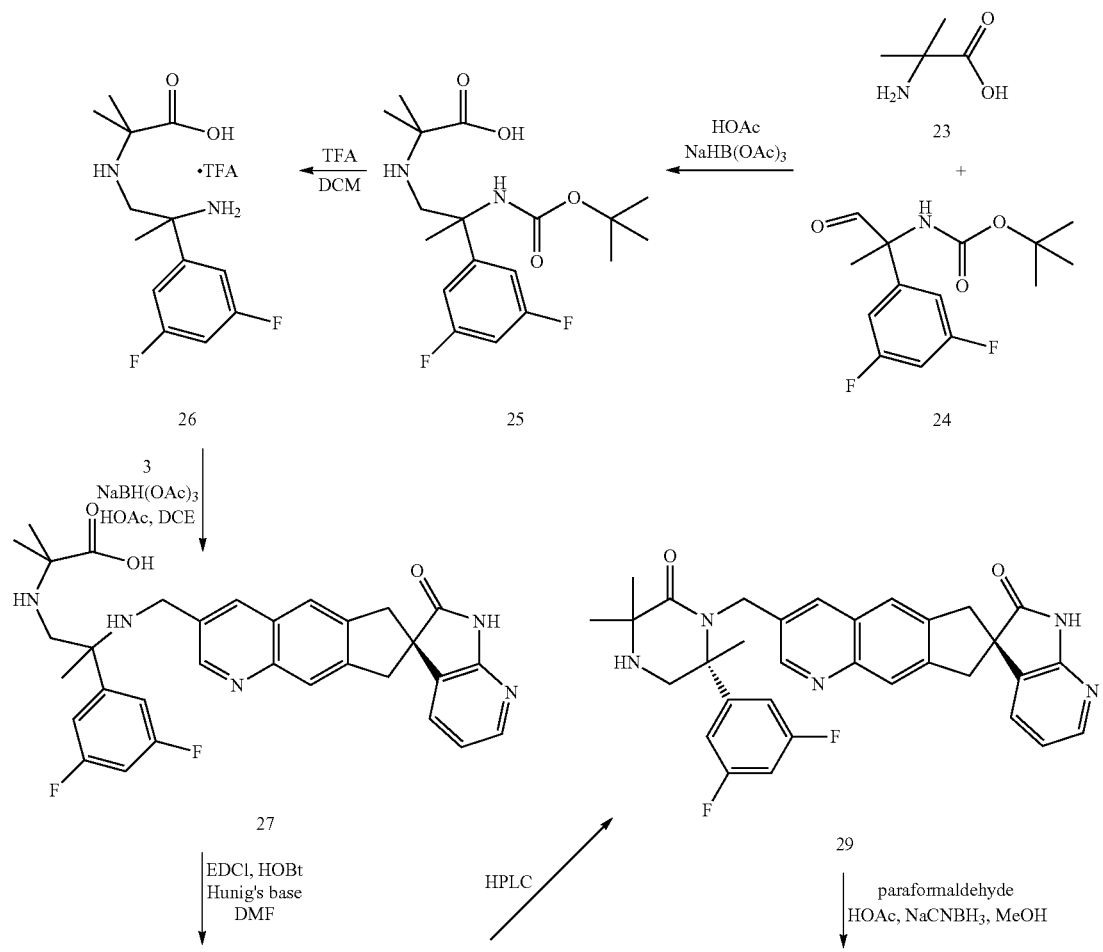

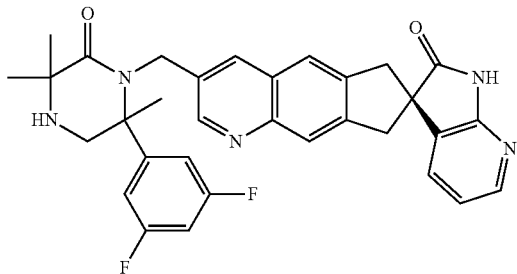

28

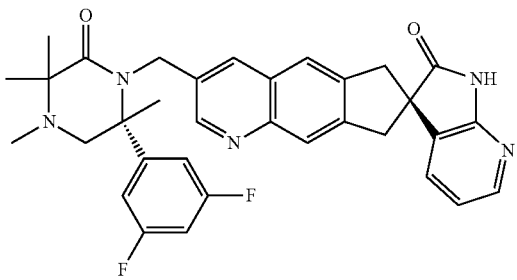

30

2-Methylalanine (compound 23) and aldehyde 24 (U.S. Patent Application Publication No. US 2007/0265225) can react, in HOAc, with sodium triacetoxyborohydride, at ambient temperature to give the acid 25. The tert-butyl carbamate of 25 can be removed by the action of TFA in DCM to provide the TFA salt 26. Similar to Scheme 5, the primary amine is selectively alklyated with aldehyde 3 (Intermediate 1) using sodium triacetoxyborohydride and HOAc, in DCM, to yield diastereomeric mixture 27. This carboxylic acid can by cyclized using EDCI, HOBt and Hunig's base, in DMF, to give the claimed compound 28. This mixture of diastereomers can separated by a variety of methods, in this case HPLC, to yield the preferred isomer 29. The secondary amine of 29 can be methylated employing paraformaldehyde, HOAc and sodium cyanoborohydride, in MeOH, to give the claimed compound 30.

SCHEME 8

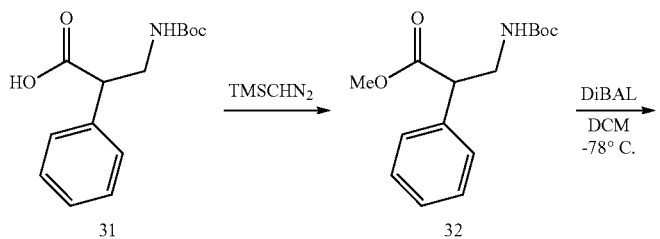

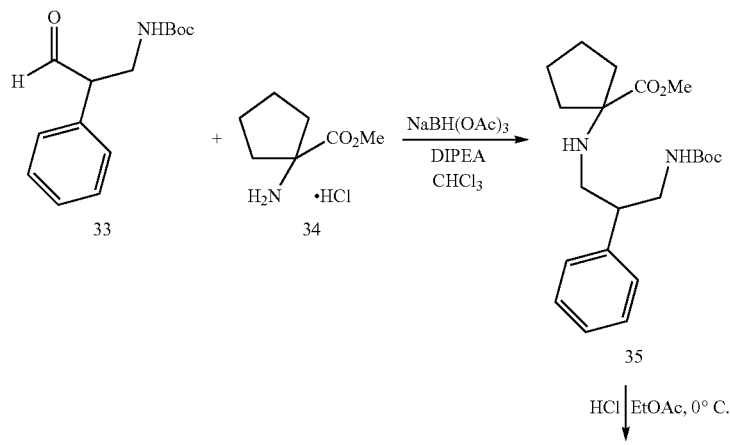

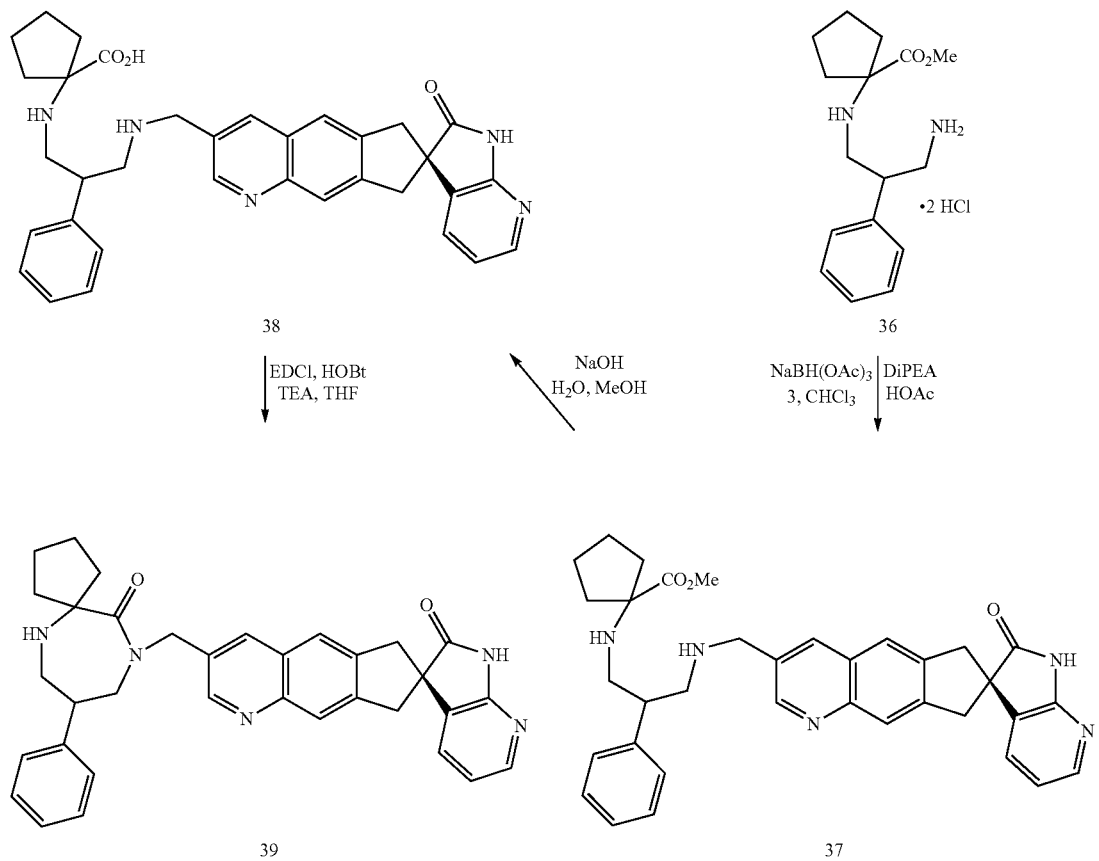

Starting from the commercially available acid 31, the methyl ester 32, was produced using TMS-diazomethane, in a mixture of methanol/chloroform (1/2 ratio). The ester was then partially reduced using diisobutylaluminum hydride, in DCM, at −78° C. to give the aldehyde 33. The amine hydrochloride of 34 was then reductively alkylated with this aldehyde using sodium triacetoxyborohydride and Hunig's base, in chloroform, at ambient temperature, to provide the secondary amine 35. The primary amine of 35, is then deprotected using anhydrous HCl, in EtOAc, at ~0° C., to give the bis-hydrochloride 36. The primary amine of 36 is selectively alklyated with aldehyde 3 (Intermediate 1) using sodium triacetoxyborohydride, Hunig's base and catalytic HOAc, in chloroform, to yield ester 37. The ester is then saponified using sodium hydroxide, in aqueous methanol, to give the acid 38. This acid is then cyclized using EDCI, HOBt and triethylamine, in THF, to give the claimed compound 39.

Although aldehyde 3 has been most frequently employed in the above schemes, one possible alternative, of many, is depicted along with its preparation, in Scheme 9.

SCHEME 9

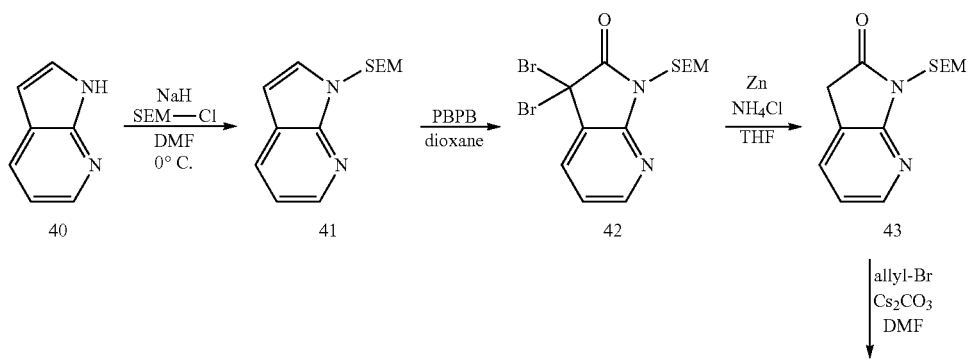

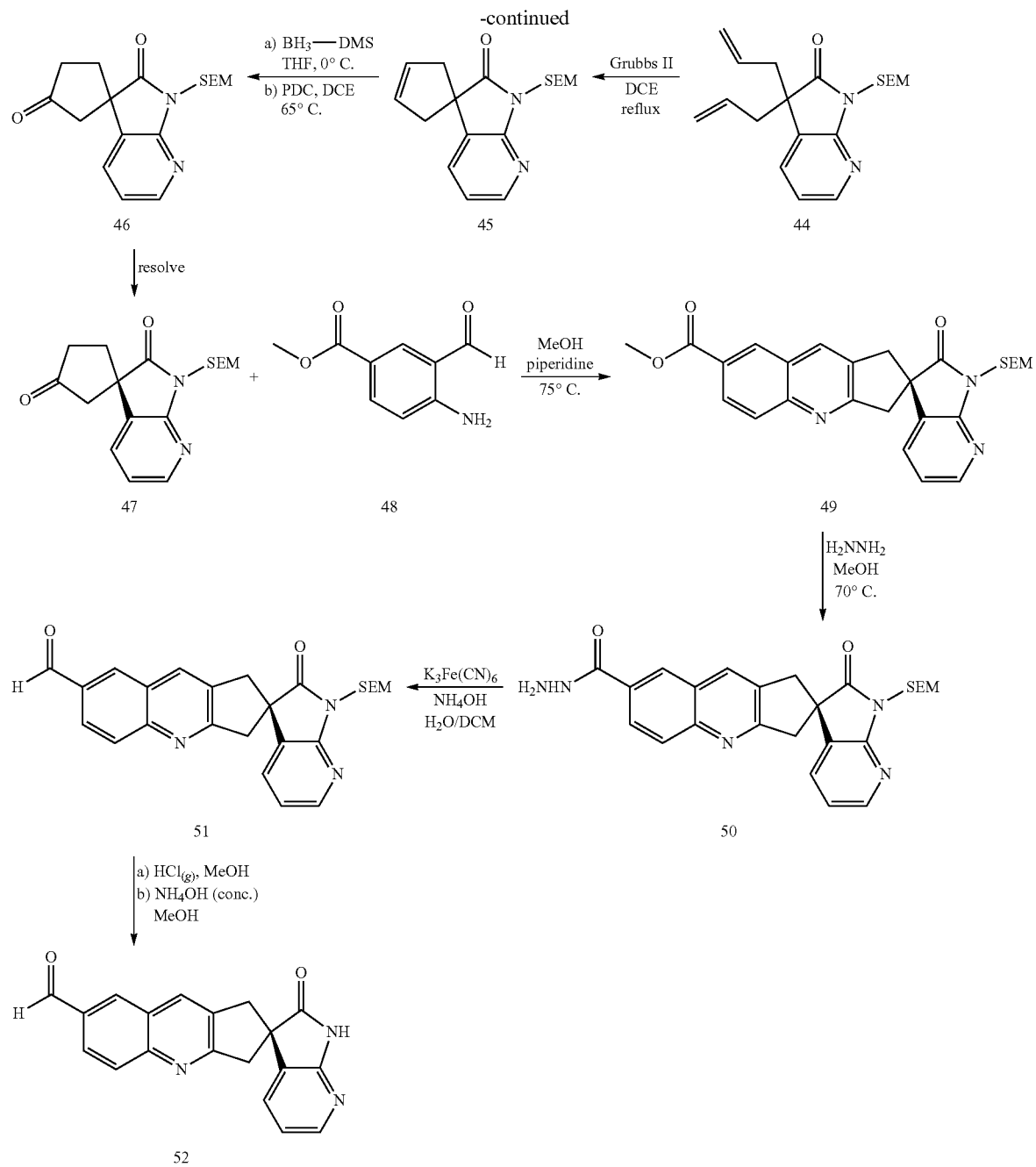

Starting from 7-azaindole (40), the nitrogen can be SEM protected using SEM-chloride subsequent to deprotonation with NaH, in DMF. Following the method of Marfat and Carter (*Tetrahedron Lett.*, 1987, 28, 4027), treatment of 41 with pyridine hydrobromide perbromide provides the dibromoazaoxindole 42. Reduction of this dibromide can be accomplished with zinc and $NH_4Cl$, in THF, to provide the corresponding azaoxindole 43. Bis-alkylation of 43 can be preformed using allyl bromide and $Cs_2CO_3$, in DMF, to give 44. Ring closing metathasis of 44 can be conducted using Grubb's second generation catalyst, in refluxing DCE, to yield the olefin 45. Oxidation of this olefin can be conducted by the two step process of hydroboration with borane-dimethylsulfoxide, in THF, followed by oxidation with PDC, in DCE, to give the racemic ketone 46. This ketone can be resolved by a number of procedures, one of which is chiral SFC eluting with liquid $CO_2$/EtOH to give the preferred (S)-ketone 47. Condensation of ketone 47, with the aldehyde 48, can be accomplished using piperidine/MeOH as solvent, followed by boiling to dryness at 75° C. (essentially a melt), to give quinoline ester 49. This ester can be converted to the acyl hydrazide, by heating with anhydrous hydrazine, in MeOH, to 70° C., giving 50. Compound 50, can then be reduced to aldehyde 51 using potassium ferricyanide, ammonium hydroxide, in a water/DCM mixture. Removal of the SEM protecting group can be accomplished by using anhydrous hydrogen chloride in MeOH, to give a hemi-aminal, which is then further deprotected using concentrated aqueous ammonium hydroxide in MeOH, to give aldehyde 52 (Intermediate 14).

Of more general scope are the structures appearing in the following schemes, which describe in more general terms methods, reagents and conditions which may be used to prepare compounds of the present invention.

SCHEME 10

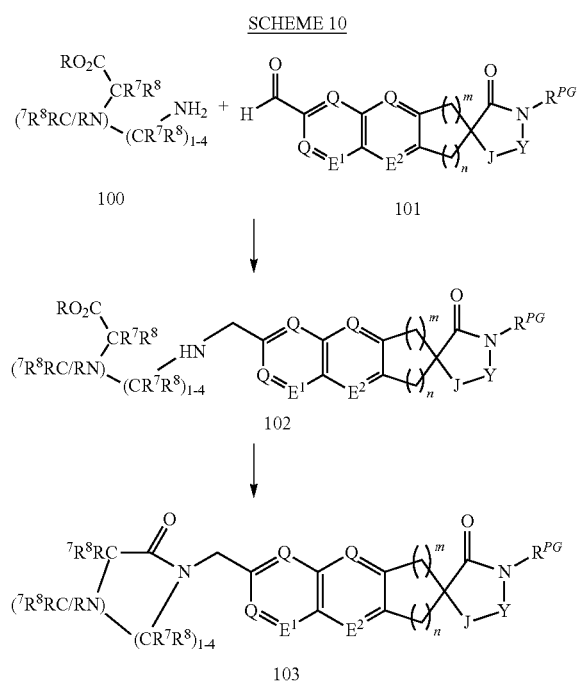

Scheme 10 shows how amino acids (R=H) or amino esters (R≠H) of general structure 100, commercially available or prepared by know methods, can be reductively alkylated, selectively on the primary nitrogen, in preference to a secondary nitrogen (if present), using an appropriate reductant, such as NaHB(OAc)$_3$ or sodium cyanoborohydride, in a solvent such as DCE, chloroform or DCM, either in the presence or absence of a general acid catalyst, such as HOAc, to give the secondary amines 102. Cyclization of 102 to the claimed compounds 103 can be achieved under a variety of conditions. For example, heating 102 in the temperature range of 30 to 200° C., in an appropriate solvent, such as toluene or xylene, optionally in the presence of an acid catalyst, such as HOAc or TFA, can afford cyclication products 103. Alternatively, when R=H, standard peptide coupling conditions, such as EDCI/HOBt or HATU, in an appropriate solvent such as DMF, DCM or THF, in the presence of a base as needed, may be employed to effect cyclization to the claimed compounds 103. Esters of 102 (R≠H), can be transformed to the necessary carboxylic acid needed for the above mentioned peptide coupling conditions using a variety of reagents, such as aqueous sodium hydroxide, potassium hydroxide or potassium carbonate, in an appropriate solvent, such as MeOH, THF or DMF.

SCHEME 11

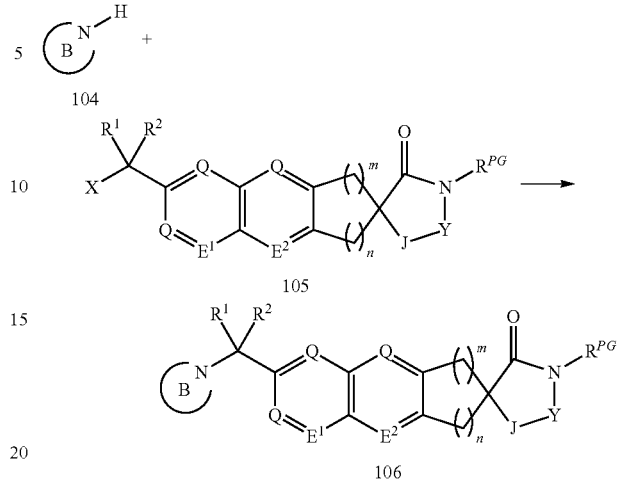

Alternatively, the electrophilic reagent 105 (where X=halogen, OTs, OTf, etc.) can be used to alkylate sufficiently nucleophilic "B"-rings (104 as previously defined herein). Examples of 104 "B"-rings include, but are not limited to, hydantoins, lactams, cyclic ureas ketopiperazines, piperidines and azapines. While some heterocycles of general structure 104 will be nucleophilic enough to affect this alkylation in an appropriate solvent, such as DMF, THF or DMSO, at a temperature ranging from −10 to +150° C., others will require activation by a strong base, such as sodium hydride or potassium tert-butoxide.

SCHEME 12

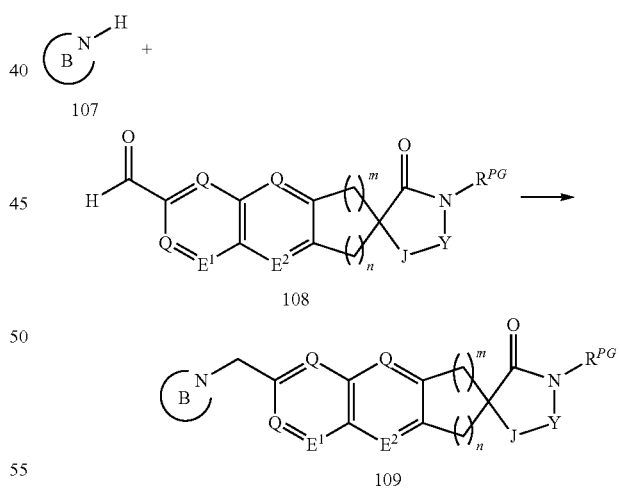

Additionally, appropriate "B"-rings (107 as previously defined herein), such as, but not limited to, piperidines, piperazines, pyrrolidines and morpholines can be reductively alkylated with aldehydes of general structure 108, using reductants, such as NaHB(OAc)$_3$ or sodium cyanoborohydride, in appropriate solvents such as chloroform, HOAc, MeOH, or DCM, either in the presence or absence of an acid catalyst, such as HOAc.

Simple modifications of these routes, including different protecting group strategies, application of well-precedented methodology, and the use of starting materials and reagents other than those described in the forgoing schemes, may be used to provide other intermediates and claimed compounds.

In some cases the final product may be further modified, for example, by manipulation of substituents. These manipulations may include, but are not limited to, reduction, oxidation, alkylation, acylation, and hydrolysis reaction which are commonly known to those skilled in the art. Moreover, in some cases the order of carrying out the foregoing reactions schemes may be varied to facilitate the reaction or to avoid unwanted reaction products. The following examples are provided so that the invention might be more fully understood. These examples are illustrative only and should not be construed as limiting the invention in any way.

The methodology shown in these schemes is not meant to limit the scope of the invention, but only to give representative examples and intermediates. Related intermediates and examples bearing a variety of substituents may be prepared by employing appropriately substituted starting materials or by derivatization of any intermediates and/or final products as desired by methods known in the art. Resolutions may be affected by other methodologies, such as fractional crystallization or diastereomeric salts, and it may be carried out on other synthetic intermediates or on the final products. Alternatively, an asymmetric synthesis of a key intermediate could be used to provide an enantiomerically enriched final product.

INTERMEDIATES AND EXAMPLES

The following examples are provided so that the invention might be more fully understood. These examples are illustrative only and should not be construed as limiting the invention in any way.

Intermediate 1

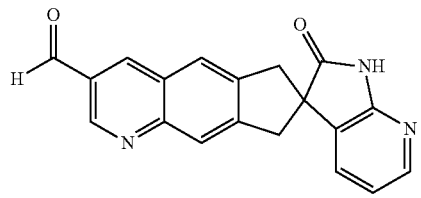 [SMILES: O=Cc1cnc2cc3c(cc2c1)CC1(C3)C(=O)Nc2ncccc21]

2'-Oxo-1',2',6,8-tetrahydrospiro[cyclopenta[g]quinoline-7,3'-pyrrolo[2,3-b]pyridine]-3-carbaldehyde Title compound was prepared according to known literature (International Patent Application Publication No. WO 2007/061677) methods, affording either enantiomer or a racemic mix as needed.

Intermediate 2

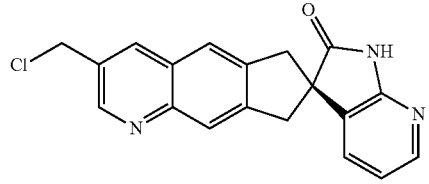 [SMILES: O=C1Nc2ncccc2[C@@]12Cc1cc3cc(CCl)cnc3cc1C2]

(7S)-3-(Chloromethyl)-6,8-dihydrospiro[cyclopenta[g]quinoline-7,3'-pyrrolo[2,3-b]pyridin]-2'(1'H)-one Step A. (7S)-3-(Hydroxymethyl)-6,8-dihydrospiro[cyclopenta[g]quinoline-7,3'-pyrrolo[2,3-b]pyridin]-2'(1'H)-one To a stirred suspension of (7S)-2'-oxo-1',2',6,8-tetrahydrospiro[cyclopenta[g]quinoline-7,3'-pyrrolo[2,3-b]pyridine]-3-carbaldehyde (1.79 g, 5.68 mmol, described in Intermediate 1) in a mixture of MeOH (30 mL) and $CH_2Cl_2$ (10 mL) was added sodium borohydride (322 mg, 8.52 mmol). The resulting mixture was stirred at ambient temperature for 48 h, with additional sodium borohydride (322 mg, 8.52 mmol) added at 16 and 20 h. The solvents were removed in vacuo and the residue was partitioned between saturated aqueous $NaHCO_3$ (100 mL) and $CH_2Cl_2$ (100 mL). The aqueous layer was extracted further with $CH_2Cl_2$ (2×100 mL). The combined organic extracts were dried over $Na_2SO_4$, filtered, and concentrated in vacuo. The crude product was purified by silica gel chromatography, eluting with a gradient of $CH_2Cl_2$:$MeOH$:$NH_4OH$—100:0:0 to 95:5:1, to give the title compound. MS: m/z=318 (M+1).

Step B. (7S)-3-Chloromethyl)-6 8-dihydrospiro[cyclopenta[g]quinoline-7,3'-pyrrolo[2,3b]-pyridin]-2'(1'H)-one To a stirred solution of (7S)-3-(hydroxymethyl)-6,8-dihydrospiro[cyclopenta[g]quinoline-7,3'-pyrrolo[2,3-b]pyridin]-2'(1'H)-one from Step A (970 mg, 3.06 mmol) in $CH_2Cl_2$ (30 mL) was added thionyl chloride (2.23 mL, 30.1 mmol) and the resulting mixture was stirred at ambient temperature for 2 h, then concentrated in vacuo. The residue was partitioned between saturated aqueous $NaHCO_3$ (30 mL) and $CH_2Cl_2$ (30 mL). The layers were separated and the aqueous layer was extracted further with $CH_2Cl_2$ (2×30 mL). The combined organic extracts were dried over $Na_2SO_4$, filtered, and concentrated in vacuo to give the title. MS: m/z=336 (M+1).

Intermediate 3

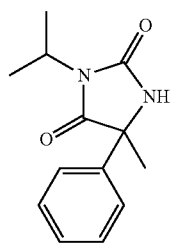 [SMILES: CC(C)N1C(=O)NC(C)(c2ccccc2)C1=O]

(±)-3-Isopropyl-5-methyl-5-phenylimidazoline-2,4-dione

To a stirred solution of (±)-5-methyl-5-phenylhydantoin (3.0 g, 15.7 mmol) in DMF (20 mL) was added potassium carbonate (2.6 g, 18.9 mmol) and 2-iodopropane (3.2 g, 18.9 mmol). The reaction was stirred at ambient temperature for 18 h and then partitioned between EtOAc (100 mL) and $H_2O$ (100 mL). The layers were separated and the aqueous phase was extracted further with EtOAc (2×100 mL). The combined organic extracts were washed with brine (100 mL), dried over MgSO₄, filtered and concentrated under reduced pressure. The crude product was purified by silica gel chromatography, eluting with a gradient of hexane:EtOAc—75:25 to 50:50, to give the title compound. MS: m/z=233 (M+1).

Essentially following analogous procedures to those outlined for Intermediate 3 or the referenced literature, the compounds listed in Table I were prepared. The requisite starting materials were commercially available, described in the literature, or readily synthesized by one skilled in the art of organic synthesis. In some cases, straightforward protecting group strategies were applied, or chiral resolutions were performed.

TABLE 1

| Intermediate | Structure | MS (M + 1) | Procedure |
|---|---|---|---|
| 4 | 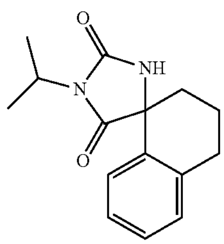 [SMILES: CC(C)N1C(=O)NC2(CCCc3ccccc32)C1=O] | 259 | Intermediate 3 |
| 5 | 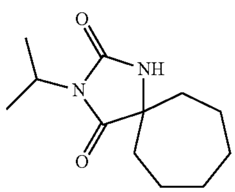 [SMILES: CC(C)N1C(=O)NC2(CCCCCC2)C1=O] | 225 | Intermediate 3 |
| 6 | 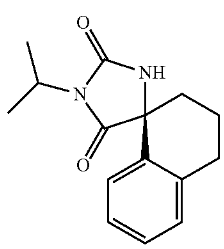 [SMILES: CC(C)N1C(=O)N[C@]2(CCCc3ccccc32)C1=O] | 259 | Intermediate 3 |
| 7 | 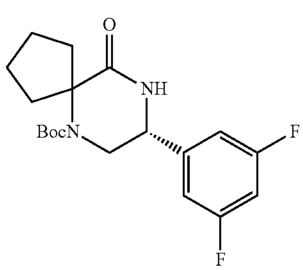 [SMILES: CC(C)(C)OC(=O)N1C[C@@H](c2cc(F)cc(F)c2)NC(=O)C12CCCC2] | 367 | U.S. Patent Application Publication No. US 2007/0265225 |
| 8 | 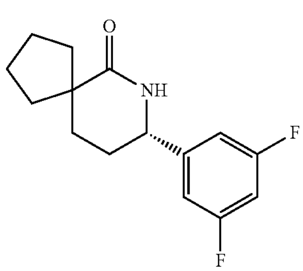 [SMILES: O=C1N[C@H](c2cc(F)cc(F)c2)CCC12CCCC2] | 266 | U.S. Patent Application Publication No. US 2007/0265225 |
| 9 | | 381 | U.S. Patent Application Publication No. US 2007/0265225 |
| 10 | | 409 | U.S. Patent Application Publication No. US 2007/0265225 |
| 11 | | 295 | U.S. Patent Application Publication No. US 2007/0265225 |
| 12 | | 337 | U.S. Patent Application Publication No. US 2007/0265225 |

Intermediate 13

2-(2-Chlorophenyl)-1,3-diazaspiro[4.4]non-1-en-4-one

Step A.
N-[1-(Aminocarbonyl)cyclopentyl]-2-chlorobenzamide

To a stirred solution of 1-aminocyclopentanecarboxamide hydrochloride (0.46 g, 2.79 mmol) in DCM (4 mL), cooled to 0° C., were added 2-chlorobenzoyl chloride (0.73 g, 4.19 mmol) and triethylamine (0.97 mL, 6.99 mmol). After stirring for 3 h, the precipitate in the reaction mixture was filtered to give the title compound.

Step B. 2-(2-Chlorophenyl)-1,3-diazaspiro[4.4]non-1-en-4-one

Into a solution of N-[1-(aminocarbonyl)cyclopentyl]-2-chlorobenzamide from Step A (0.51 g, 1.912 mmol) in methanol (10 mL) was added NaOH (1.15 mL, 5 N). This solution was heated at 90° C. for 2.5 h. After allowing the reaction mixture to cool, the bulk of the solvent was removed in vacuo to give a residue, which was then neutralized by the addition of 1 N HCl and diluted with DCM. The layers were separated and the aqueous layer was extracted with an additional volume of DCM. The combined organics were dried over sodium sulfate, filtered, and concentrated in vacuo to yield the title compound as a white solid. MS: m/z=249 (M+1).

Intermediate 14

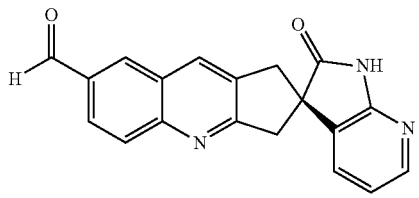 [SMILES: O=Cc1ccc2nc3c(cc2c1)C[C@@]1(C3)C(=O)Nc2ncccc21]

(2S)-2'-Oxo-1,1',2',3-tetrahydrospiro[cyclopenta[b]quinoline-2,3'-pyrrolo[2,3-b]pyridine]-7-carbaldehyde Step A. 1-{[2-(Trimethylsilyl)ethoxy]methyl}-1H-pyrrolo[2,3-b]pyridine Sodium hydride (60% dispersion in mineral oil; 16.2 g, 0.404 mol) was added in portions over 25 min to a solution of 7-azaindole (39.8 g, 0.337 mol) in DMF (200 mL) at 0° C. and the mixture was stirred for 1 h. 2-(Trimethylsilyl)ethoxymethyl chloride (71.8 mL, 0.404 mol) was then added slowly over 15 min, keeping the temperature of the reaction mixture below 10° C. After 1 h, the reaction was quenched with water (500 mL) and the mixture was extracted with $CH_2Cl_2$ (5×300 mL). The combined organic layers were washed with saturated brine, dried over $MgSO_4$, filtered, concentrated and dried under high vacuum to give the title compound. MS: m/z=249 (M+1).

Step B. 3,3-Dibromo-1-{[2-(trimethylsilyl)ethoxy]methyl}-1,3-dihydro-2H-pyrrolo[2,3-b]pyridin-2-one A solution of 1-{[2-(trimethylsilyl)ethoxy]methyl}-1H-pyrrolo[2,3-b]pyridine from Step A (43.1 g, 0.1735 mol) in dioxane (300 mL) was added dropwise over 30 min to a suspension of pyridine hydrobromide perbromide (277 g, 0.8677 mol) in dioxane (300 mL). The reaction was stirred at ambient temperature using an overhead mechanical stirrer to produce two layers. After 60 min, the reaction was quenched with water (300 mL) and extracted with EtOAc (500 mL). The aqueous layer was extracted further with EtOAc (2×300 mL) and the combined organic layers were washed with $H_2O$ (4×300 mL; the final wash was pH 5-6), then brine (300 mL), dried over $MgSO_4$, filtered and concentrated in vacuo. The crude product was immediately dissolved in $CH_2Cl_2$ and the solution filtered through a plug of silica, eluting with $CH_2Cl_2$ until the dark red color had completely eluted from the plug. The filtrate was washed with saturated aqueous $NaHCO_3$ (400 mL), then brine (400 mL), dried over $MgSO_4$ filtered, and concentrated in vacuo to give the title compound. MS: m/z=423 (M+1).

Step C. 1-{[2-(Trimethylsilyl)ethoxy]methyl}-1,3-dihydro-2H-pyrrolo[2,3-b]pyridin-2-one Zinc (100 g, 1.54 mol) was added to a solution of 3,3-dibromo-1-{[2-(trimethylsilyl)ethoxy]methyl}-1,3-dihydro-2H-pyrrolo[2,3-b]pyridin-2-one (65 g, 0.154 mol) in THF (880 mL) and saturated aqueous $NH_4Cl$ (220 mL). After 3 h, the reaction mixture was filtered and concentrated in vacuo. The residue was partitioned between EtOAc and $H_2O$ which resulted in the formation of a white precipitate. Both layers were filtered through a Celite pad and the layers were separated. The aqueous layer was washed with EtOAc (2×500 mL) and the combined organic layers were washed with $H_2O$, dried over $MgSO_4$, filtered, and concentrated under reduced pressure. The crude product was purified by silica gel chromatography, eluting with $CH_2Cl_2$:EtOAc—90:10, to give the title compound. MS: m/z=265 (M+1).

Step D. 3,3-Diallyl-1-{[2-(trimethylsilyl)ethoxy]methyl}-1,3-dihydro-2H-pyrrolo[2,3-b]pyridin-2-one To a solution of 1-{[2-(trimethylsilyl)ethoxy]methyl}-1,3-dihydro-2H-pyrrolo[2,3-b]pyridin-2-one from Step C (1.00 g, 3.78 mmol) and cesium carbonate (3.70 g, 1.4 mmol) in DMF (10 mL) was added a solution of allyl bromide (0.720 mL, 8.32 mmol). After 6 h, the mixture was poured onto saturated $NaHCO_3$ (50 mL) and extracted with $CH_2Cl_2$ (3×30 mL). The combined organic layers were dried over $Na_2SO_4$, filtered, and concentrated in vacuo. The crude product was purified by silica gel chromatography, eluting with a gradient of hexane:EtOAc—100:0 to 50:50, to give the title compound. MS: m/z=345 (M+1).

Step E. 1'-{[2-(Trimethylsilyl)ethoxy]methyl}spiro[cyclopent-3-ene-1,3'-pyrrolo[2,3-b]pyridine]-2'(1'H)-one A mixture of 3,3-diallyl-1-{[2-(trimethylsilyl)ethoxy]methyl}-1,3-dihydro-2H-pyrrolo[2,3-b]pyridin-2-one from Step D (1.02 g, 2.96 mmol) and Grubbs second generation catalyst (37 mg, 0.045 mmol) in DCE (60 mL) was heated at reflux for 3.5 h. The mixture was concentrated in vacuo and purified by silica gel chromatography, eluting with a gradient of hexane:EtOAc—100:0 to 75:25, to give the title compound. MS: m/z=317 (M+1).

Step F. (1S)-1'-{[2-(Trimethylsilyl)ethoxy]methyl}-3H-spiro[cyclopentane-1,3'-pyrrolo[2,3-b]pyridine]-2',3(1'H)-dione Borane-methyl sulfide complex (0.984 mL, 1.97 mmol, 2M in THF) was added drop wise to a solution of 1'-{[2-

(trimethylsilyl)ethoxy]methyl}spiro[cyclopent-3-ene-1,3'-pyrrolo[2,3-b]pyridin]-2'(1'H)-one from Step E (208 mg, 0.656 mmol) in THF (3 mL) at 0° C. and the solution was slowly warmed to RT over 3.5 h. The reaction mixture was carefully quenched by the slow addition of water until hydrogen evolution ceased and then concentrated in vacuo. The resulting solid was dissolved in DMF (1 mL) and DCE (0.5 mL) and added drop wise to a suspension of PDC (740 mg, 1.97 mmol) in DCE (5 mL) at ambient temperature. The reaction mixture was heated at 65° C. for 21 h, with additional PDC (500 mg) added after 18 h. Celite was added to the reaction mixture until clumping occurred, and then it was diluted with $Et_2O$ (50 mL). The mixture was filtered through a Celite plug, rinsing with additional $Et_2O$ (4×50 mL) and the filtrate concentrated in vacuo. The crude product was purified by silica gel chromatography, eluting with a gradient of hexane:EtOAc—100:0 to 50:50. This racemic mixture was resolved using SFC, eluting with $CO_2$(/EtOH to give the title compound. MS: m/z=333 (M+1).

Step G. Methyl (2S)-2'-oxo-1'-{[2-(trimethylsilyl)ethoxy]methyl}-1,1',2',3-tetrahydrospiro[cyclopenta[b]quinoline-2,3'-pyrrolo[2,3-b]pyridine]-7-carboxylate To a solution of (1S)-1'-{[2-(trimethylsilyl)ethoxy]methyl}-3H-spiro[cyclopentane-1,3'-pyrrolo[2,3-b]pyridine]-2',3(1'H)-dione from step F (375 mg, 1.13 mmol) and methyl 4-amino-3-formylbenzoate (202 mg, 1.13 mmol) in MeOH (5 mL) was added piperidine (192 mg, 2.26 mmol). The mixture was then place into a 75° C. bath, open to the air, and allowed to boil dry. Reaction progress was occasionally checked by adding MeOH (~3 mL) prior to removal of an aliquot for LCMS analysis. After heating for 22 hours, the reaction was allowed to cool before being diluted with DCM (minimal amount) and applied directly to a silica gel column, eluting with a gradient of hexane:EtOAc—80:20 to 30:70 (pausing at 60:40) to give the title compound. MS: m/z=476 (M+1).

Step H. (2S)-2'-oxo-1'-{[2-(Trimethylsilyl)ethoxy]methyl}-1,1',2',3-tetrahydrospiro[cyclopenta[b]quinoline-2,3'-pyrrolo[2,3-b]pyridine]-7-carbohydrazide To a solution of methyl (2S)-2'-oxo-1'-{[2-(trimethylsilyl)ethoxy]methyl}-1,1',2', 3-tetrahydrospiro[cyclopenta[b]quinoline-2,3'-pyrrolo[2,3-b]pyridine]-7-carboxylate from Step G (317 mg, 0.667 mmol) in MeOH (1 mL) was added hydrazine (1.0 mL, 32 mmol). The reaction was sealed and then heated to 70° C. for 18 hours. After cooling to ambient temperature, the bulk of the solvent was removed in vacuo. The residue was diluted with DCM (50 mL) and water (20 mL). The organics were then successively washed with water, half-saturated brine and brine before being dried over sodium sulfate. The organics were then filtered, concentrated in vacuo to give the title compound. MS: m/z=476 (M+1).

Step I. (2S)-2'-Oxo-1'-{[2-(trimethylsilyl)ethoxy]methyl}-1,1', 2',3-tetrahydrospiro[cyclopenta[b]quinoline-2,3'-pyrrolo[2,3-b]pyridine]-7-carbaldehyde To a rapidly stirred solution of (2S)-2'-oxo-1'-{[2-(trimethylsilyl)eth-oxy]methyl}-1,1',2',3-tetrahydrospiro[cyclopenta[b]quinoline-2,3'-pyrrolo[2,3-b]pyridine]-7-carbohydrazide from Step H (317 mg, 0.667 mmol) in DCM (6.8 mL) was added water (2.7 mL) plus concentrated aqueous $NH_4OH$ (0.6 mL) and lastly potassium ferricyanide (549 mg, 1.67 mmol). After 4.5 hours the reaction was diluted with water (20 mL) and DCM (40 mL). The aqueous layer was extracted once with DCM (20 mL). The combined organics were washed successively with water then half-saturated brine and then dried over sodium sulfate. The organics were then filtered, concentrated in vacuo, and applied to a silica gel column for purification, eluting with a gradient of $CH_2Cl_2$:MeOH—99:1 to 90:10. Clean product-containing fractions were pooled and concentrated in vacuo to give the title compound. MS: m/z=446 (M+1).

Step J. (2S)-2e-Oxo-1,1',2',3-tetrahydrospiro[cyclopenta[b]quinoline-2,3'-pyrrolo[2,3-b]pyridine]-7-carbaldehyde To a solution of (2S)-2'-oxo-1'-{[2-(trimethylsilyl)ethoxy]methyl}-1,1', 2',3-tetrahydrospiro[cyclopenta[b]quinoline-2,3'-pyrrolo[2,3-b]pyridine]-7-carbaldehyde from Step (142 mg, 0.320 mmol) in MeOH (17 mL) was introduced gaseous anhydrous hydrogen chloride by bubbling the gas through the solution until the MeOH was saturated and mildly warmed. This saturation with HCl was repeated once again after 3 hours then the sealed reaction was allowed to sit at ambient temperature for 19 hours. The solution was then purged with a stream of nitrogen for 20-30 minutes, before being concentrated in vacuo. MeOH (50 mL) was added, then removed in vacuo, repeating this addition/concentration twice to remove excess HCl. The residue was dissolved in MeOH (17 mL) prior to the addition of concentrated aqueous $NH_4OH$ (0.7 mL). After 20 minutes the MeOH was removed in vacuo, fresh MeOH (50 mL) was added then remove in vacuo to produce a residue. This residue was dissolved in water (1.35 mL) plus 4 drops on conc. $H_2SO_4$. This aqueous solution was transferred to an Erlenmeyer flask using water (3 mL) and 2 more drops of conc. $H_2SO_4$. Slow neutralization with aqueous NaOH (1 M, ~2.5 mL) provided a solid which was filtered, washed with water, air dried and vacuum dried to give the title compound. MS: m/z=316 (M+1).

EXAMPLE 1

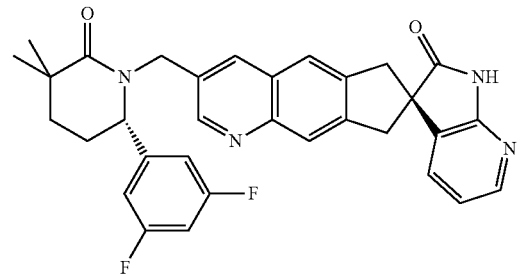 [SMILES: CC1(C)CC[C@@H](c2cc(F)cc(F)c2)N(Cc2cnc3cc4c(cc3c2)C[C@@]2(C4)C(=O)Nc3ncccc32)C1=O]

(7S)-3-{[(6S)-6-(3,5-Difluorophenyl)-3,3-dimethyl-2-oxopiperidin-1-yl]methyl}-6,8-dihydrospiro[cyclopenta[g]quinoline-7,3'-pyrrolo[2,3-b]pyridin]-2'(1'H)-one

Step A. Ethyl (5S)-5-amino-5-(3,5-difluorophenyl)-2,2-dimethylpentanoate

To a solution of ethyl (5S)-5-{[(S)-tert-butylsulfinyl]amino}-5-(3,5-difluorophenyl)-2,2-dimethylpentanoate (113 mg, 0.289 mmol, prepared by direct analogy to the methyl ester version according to U.S. Patent Application Publication No. US 2007/0265225) in MeOH (6 mL), cooled to 0° C., was added excess anhydrous, gaseous HCl over 1 minute via a rapid stream of bubbles. After 30 min, a stream of nitrogen was passed over the solution to remove some HCl. The reaction was then concentrated in vacuo. The residue was diluted with DCM (20 mL) and washed with saturated sodium bicarbonate (10 mL). The bicarbonate layer was subsequently extracted twice with DCM (10 mL). The combined organics were dried over sodium sulfate, filtered and concentrated in vacuo, to yield a residue, containing about 30% methyl ester, which was used without further purification. MS: m/z=286 (M+1).

Step B. Ethyl (5S)-5-(3,5-difluorophenyl)-2,2-dimethyl-5-({[(7S)-2'-oxo-1',2',6,8-tetrahydrospiro[cyclopenta[g]quinoline-7,3'-pyrrolo[2,3-b]pyridin]-3-yl]methyl}amino)pentanoate To a stirred solution of ethyl (5S)-5-amino-5-(3,5-difluorophenyl)-2,2-dimethylpentanoate from Step A (~82.0 mg, 0.289 mmol) and (7S)-2'-oxo-1', 2',6,8-tetrahydrospiro[cyclopenta[g]quinoline-7,3'-pyrrolo[2,3-b]pyridine]-3-carbaldehyde (91.0 mg, Intermediate 1) in dry chloroform (3 mL) was added HOAc (35 µL, 0.606 mmol). After 10 minutes, sodium triacetoxyborohydride (129 mg, 0.606 mmol) was added. After 80 minutes of stirling, the reaction mixture was diluted with DCM (30 mL) and saturated sodium bicarbonate (20 mL). The layers were separated and the aqueous layer was extracted once with DCM (20 mL). The combined organics were dried over sodium sulfate, filtered and concentrated in vacuo to provide a residue. This residue was applied to a silica gel column for purification, eluting with a gradient of CH$_2$Cl$_2$:MeOH—99:1 to 93:7. Clean product-containing fractions were pooled and concentrated in vacuo to give the title compound, which still contained about 30% of the methyl ester. MS: m/z=585 (M+1).

Step C. (7S)-3-{[(6S)-6-(3,5-Difluorophenyl)-3,3-dimethyl-2-oxopiperidin-1-yl]methyl}-6,8-dihydrospiro[cyclopenta[g]quinoline-7,3'-pyrrolo[2,3-b]pyridin]-2'(1'H)-one A solution of ethyl (5S)-5-(3,5-difluorophenyl)-2,2-dimethyl-5-({[(7S)-2'-oxo-1',2',6,8-tetrahydrospiro[cyclopenta[g]quinoline-7,3'-pyrrolo[2,3-b]pyridin]-3-yl]methyl}amino)pentanoate from Step B (131 mg, 0.224 mmol) in a 90/10 mixture of xylenes/HOAc (20 mL) was heated to 140° C. for ~22 hours. After allowing the reaction mixture to cool, the bulk of the solvent was removed in vacuo to give a residue. This residue was diluted with chloroform (50 mL) and washed with saturated sodium bicarbonate (25 mL). This aqueous layer was then extracted twice with DCM (2×30 mL). The combined organics were dried over sodium sulfate, filtered and concentrated in vacuo to provide a residue. This residue was applied to a silica gel column for purification, eluting with a gradient of CH$_2$Cl$_2$:MeOH—99:1 to 94:6. Clean product-containing fractions were pooled and concentrated in vacuo to give the title compound. MS: m/z=585 (M+1). HRMS: m/z=539.2264; calculated m/z=539.2253 for C$_{32}$H$_{29}$F$_2$N$_4$O$_2$.

EXAMPLE 2

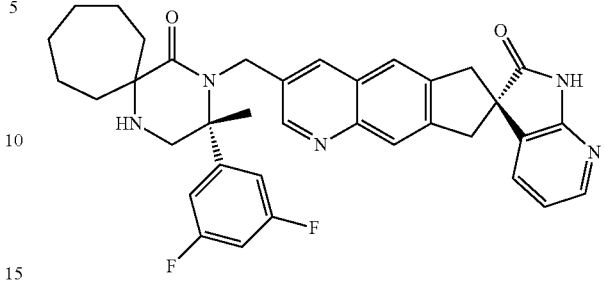

(7S)-3-{[(3R)-3-(3,5-Difluorophenyl)-3-methyl-5-oxo-1,4-diazaspiro[5.6]dodec-4-yl]methyl}-6,8-dihydrospiro[cyclopenta[g]quinoline-7,3'-pyrrolo[2,3-b]pyridin]-2'(1'H)-one Step A. tert-Butyl (3R)-3-(3,5-difluorophenyl)-3-methyl-5-oxo-4-{[(7S)-2'-oxo-1',2',6,8-tetrahydrospiro[cyclopenta[g]quinoline-7,3'-pyrrolo[2,3-b]pyridin]-3-yl]methyl}-1,4-diazaspiro[5.6]dodecane-1-carboxylate To a solution of tert-butyl (3R)-3-(3,5-difluorophenyl)-3-methyl-5-oxo-1,4-diazaspiro[5.6]dodecane-1-carboxylate (32.8 mg, 0.080 mmol, Intermediate 10) in DMF (1 mL), at ambient temperature, was added sodium hydride (60% dispersion in mineral oil; 4.3 mg, 0.11 mmol). The resulting mixture was stirred for 30 min, then (7S)-3-(chloromethyl)-6,8-dihydrospiro[cyclopenta[g]quinoline-7,3'-pyrrolo[2,3-b]pyridin]-2'(1'11)-one (18 mg, 0.054 mmol, described in Intermediate 2) was added and the resulting mixture was stirred at ambient temperature for 1 h. The reaction mixture was quenched with H$_2$O (0.1 mL) and purified by HPLC using a reversed phase C18 column and eluting with a gradient of H$_2$O:CH$_3$CN:CF$_3$CO$_2$H—90:10:0.1 to 5:95:0.1. The pure, product-containing fractions were combined and concentrated to give the title compound as the trifluoroacetate salt. MS: m/z=708 (M+1).

Step B. (7S)-3-{[(3R)-3-(3,5-Difluorophenyl)-3-methyl-5-oxo-1,4-diazaspiro[5.6]dodec-4-yl]methyl}-6,8-dihydrospiro[cyclopenta[g]quinoline-7,3'-pyrrolo[2,3-b]pyridin]-2'(1'H)-one A solution of the tert-butyl (3R)-3-(3,5-difluorophenyl)-3-methyl-5-oxo-4-{[(7S)-2'-oxo-1',2',6,8-tetrahydrospiro[cyclopenta[g]quinoline-7,3'-pyrrolo[2,3-b]pyridin]-3-yl]methyl}-1,4-diazaspiro[5.6]dodecane-1-carboxylate from Step A (20 mg, 0.028 mmol) in CH$_2$Cl$_2$ (0.7 mL) and CF$_3$CO$_2$H (0.3 mL) was aged at ambient temperature for 1 h. The reaction mixture was purified by HPLC using a reversed phase C18 column and eluting with a gradient of H$_2$O:CH$_3$CN: CF$_3$CO$_2$H—90:10:0.1 to 5:95:0.1. The pure, product-containing fractions were combined and concentrated to give the title compound as the trifluoroacetate salt. MS: m/z=608 (M+1). HRMS: m/z=608.2852; calculated m/z=608.2832 for $C_{36}H_{36}F_2N_5O_2$.

EXAMPLE 3

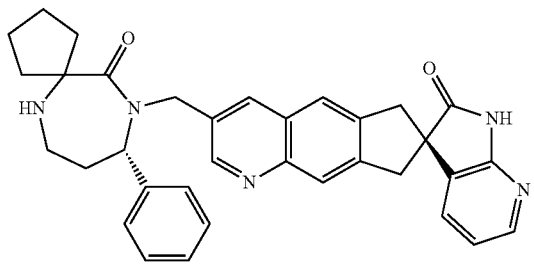 [SMILES: O=C1N(Cc2cnc3cc4c(cc3c2)C[C@@]2(C4)C(=O)Nc3ncccc32)[C@H](c2ccccc2)CCNC12CCCC2]

(7S)-3-{[(9S)-11-Oxo-9-phenyl-6,10-diazaspiro[4.6]undec-10-yl]methyl}-6,8-dihydrospiro[cyclopenta[g]quinoline-7,3'-pyrrolo[2,3-b]pyridin]-2'(1'H)-one Step A. Methyl 1-{[(3S)-3-({[(7S)-2'-oxo-1', 2',6,8-tetrahydrospiro[cyclo-penta[g]quinoline-7,3'-pyrrolo[2,3-b]pyridin]-3-yl]methyl}amino)-3-phenylpropyl]amino)cyclopentanecarboxylate To a stirred suspension of methyl-{[(3S)-3-amino-3-phenylpropyl]amino}cyclopentanecarboxylate dihydrochloride (222 mg, 0.634 mmol, prepared according to U.S. Patent Application Publication No. US 2007/0265225) and (7S)-2'-oxo-1',2', 6,8-tetrahydrospiro[cyclopenta[g]quinoline-7,3'-pyrrolo[2,3-b]pyridine]-3-carbaldehyde (200 mg, 0.634 mmol, Intermediate 1) in chloroform (16 mL) was added Hunig's base (0.222 mL, 1.27 mmol). One hour later, sodium triacetoxyborohydride (403 mg, 1.90 mmol) was added. Two hours later, the reaction was quenched by the addition of saturated sodium bicarbonate (3 mL) and the reaction was allowed to stir for an additional 30 minutes. This mixture was further diluted with water (10 mL) and chloroform (40 mL). The aqueous layer was separated and extracted once with chloroform (30 mL). The combined organics were dried over sodium sulfate, filtered and concentrated in vacuo to provide a residue. This residue was applied to a silica gel column for purification, eluting with a gradient of $CH_2Cl_2$:MeOH (10% conc. $NH_4OH$)—99:1 to 90:10. Clean product-containing fractions were pooled and concentrated in vacuo to give the title compound. MS: m/z=576 (M+1).

Step B. Potassium 1-{[(3S)-3-({[(7S)-2'-oxo-1', 2',6,8-tetrahydrospiro[cyclo-penta[g]quinoline-7,3'-pyrrolo[2,3-b]pyridin]-3-yl]methyl}amino)-3-phenylpropyl]amino}cyclopentanecarboxylate To a solution of methyl 1-{[(3S)-3-({[(7S)-2'-oxo-1',2',6,8-tetrahydrospiro[cyclo-penta[g]quinoline-7,3'-pyrrolo[2,3-b]pyridin]-3-yl]methyl}amino)-3-phenylpropyl]amino}cyclopentanecarboxylate from Step A (50. mg, 0.087 mmol) in a minimal amount of THF (5 mL) was added KOTMS (22 mg, 0.17 mmol), prior to heating to 50° C. Additional KOTMS was added as needed (~2 equiv) until very little starting material was detected in solution. The reaction was allowed to cool to ambient temperature before the THF solution was separated from the precipitated solids. Analysis of the remaining solids indicated it was 87% title compound and 13% starting material. This mixture was used without further purification in the next step. MS: m/z=562 (M+1).

Step C. (7S)-3-{[(9S)-11-oxo-9-phenyl-6,10-diazaspiro[4,6]undec-10-yl]methyl}-6,8-dihydrospiro[cyclopenta[g]quinoline-7,3'-pyrrolo[2,3-b]pyridin]-2'(1'H)-one To a solution of potassium 1-{[(3S)-3-({[(7S)-2'-oxo-1',2',6,8-tetrahydrospiro[cyclo-penta[g]quinoline-7,3'-pyrrolo[2,3-b]pyridin]-3-yl]methyl}amino)-3-phenylpropyl]amino}cyclopentanecarboxylate from step B (~50 mg, ~0.87 mmol) in DMF (4.5 mL) was added HOAt (18 mg, 0.13 mmol) and EDCI (150 mg, 0.80 mmol, in 4 portions). After 5 hours at ambient temperature, the reaction mixture was placed into a 60° C. bath for 16 hours. After the reaction was allowed to cool back to ambient temperature, the bulk of the DMF was removed in vacuo, before being diluted with chloroform (20 mL) and half-saturated sodium bicarbonate (5 mL). The aqueous layer was separated and extracted once with chloroform. The combined organics were dried over sodium sulfate, filtered and concentrated in vacuo to provide a residue. This residue was applied to a silica gel column for purification, eluting with a gradient of $CH_2Cl_2$:MeOH—99:1 to 92:8. Product-containing fractions were pooled and concentrated in vacuo to give the title compound. MS: m/z=544 (M+1). HRMS: m/z=544.2762; calculated m/z=544.2707 for $C_{34}H_{34}N_5O_2$.

EXAMPLE 4

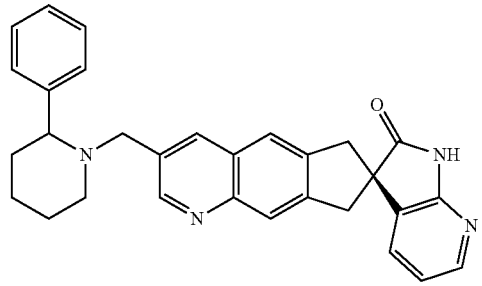 [SMILES: O=C1Nc2ncccc2[C@@]12Cc1cc3cc(CN4CCCCC4c4ccccc4)cnc3cc1C2]

(7S)-3-[(2-Phenylpiperidin-1-yl)methyl]-6,8-dihydrospiro[cyclopenta[g]quinoline-7,3'-pyrrolo[2,3-b]pyridin]-2'(1'H)-one To a suspension of aldehyde (40.0 mg, 0.127 mmol) in $CHCl_3$ (2 mL) was added HOAc (approximately 50 uL) and 2-phenylpiperidine (30.7 mg, 0.190 mmol). After 10 minutes, the reaction becomes homogeneous, at which time sodium triacetoxyborohydride (56.5 mg, 0.266 mmol) was added and stirred at ambient temperature for 22 hours. The crude reaction solution was purified by silica gel chromatography, eluting with a gradient of MeOH (10% $NH_4OH$):$CH_2Cl_2$—1:99 to 10:90, to provide a mixture of starting aldehyde and desired product. PS-Trisamine was added to this mixture in DCM (2.5 mL) and agitated for 3 hours. Filtration, followed by concentration in vacuo afforded the title compound. MS: m/z=461 (M+1). HRMS: =461.2352; calculated m/z=461.2336 for $C_{30}H_{29}N_4O$.

Essentially following analogous procedures to those outlined for Example 2 and using Intermediates 4-13 the following examples were prepared. In some cases, straightforward protecting group strategies were applied, or chiral resolutions were performed.

| Example | Structure | MS (M + 1) |
|---|---|---|
| 5 | 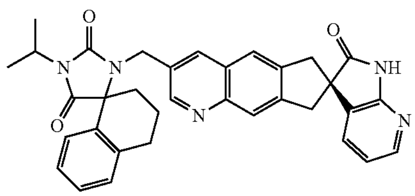 [SMILES: CC(C)N1C(=O)N(Cc2cnc3cc4c(cc3c2)C[C@@]2(C4)C(=O)Nc3ncccc32)C2(CCCc3ccccc32)C1=O] | 558 |
| 6 | 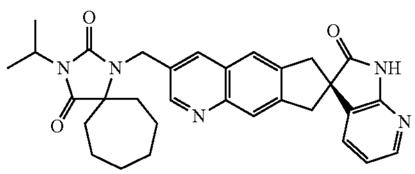 [SMILES: CC(C)N1C(=O)N(Cc2cnc3cc4c(cc3c2)C[C@@]2(C4)C(=O)Nc3ncccc32)C2(CCCCCC2)C1=O] | 524 |
| 7 | 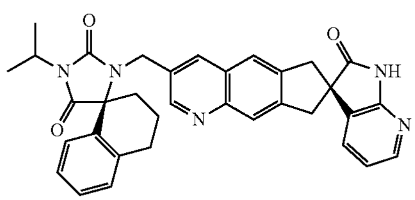 [SMILES: CC(C)N1C(=O)N(Cc2cnc3cc4c(cc3c2)C[C@@]2(C4)C(=O)Nc3ncccc32)[C@]2(CCCc3ccccc32)C1=O] | 558 |
| 8 | 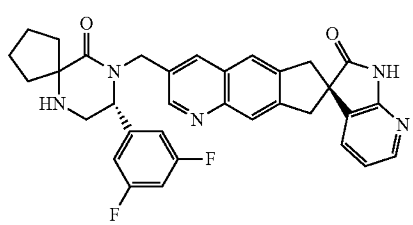 [SMILES: O=C1N(Cc2cnc3cc4c(cc3c2)C[C@@]2(C4)C(=O)Nc3ncccc32)[C@H](c2cc(F)cc(F)c2)CNC12CCCC2] | 566 |
| 9 | 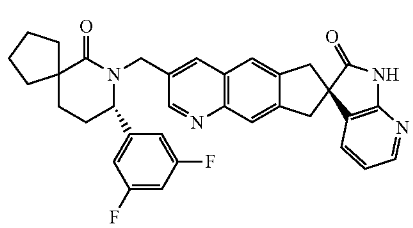 [SMILES: O=C1N(Cc2cnc3cc4c(cc3c2)C[C@@]2(C4)C(=O)Nc3ncccc32)[C@H](c2cc(F)cc(F)c2)CCC12CCCC2] | 565 |
| 10 | 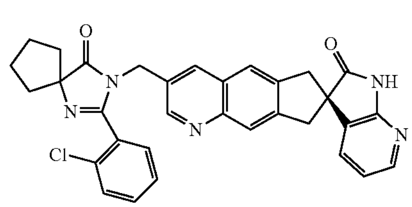 [SMILES: O=C1N(Cc2cnc3cc4c(cc3c2)C[C@@]2(C4)C(=O)Nc3ncccc32)C(c2ccccc2Cl)=NC12CCCC2] | 548 |
| 11 | | 580 |
| 12 | | 532 |
| 13 | | 594 |
| 14 | | 536 |

Essentially following analogous procedures to those outlined for Example 3, but using the slightly modified starting material: benzyl 1-{[(3S)-3-amino-3-(3,5-difluorophenyl) propyl]amino}cyclopentanecarboxylate dihydrochloride and either Intermediate 1 or Intermediate 14, the following examples were prepared. The requisite starting materials were commercially available, described in the literature, or readily synthesized by one skilled in the art of organic synthesis. In some cases, straightforward protecting group strategies were applied, or chiral resolutions were performed.

| Example | Structure | MS (M + 1) |
|---|---|---|
| 15 | 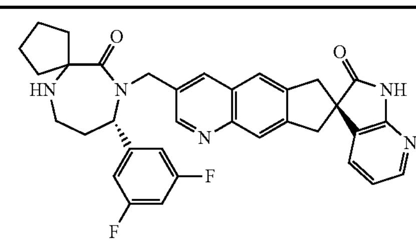 | 580 |

-continued

| Example | Structure | MS (M + 1) |
|---|---|---|
| 16 | 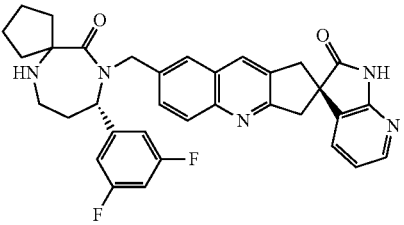 [SMILES: O=C1N(Cc2ccc3nc4c(cc3c2)C[C@@]2(C4)C(=O)Nc3ncccc32)[C@H](c2cc(F)cc(F)c2)CCNC12CCCC2] | 580 |

Essentially following analogous procedures to those outlined for Example 4 the following example was prepared. The requisite starting materials were commercially available, described in the literature, or readily synthesized by one skilled in the art of organic synthesis. In some cases, straightforward protecting group strategies were applied, or chiral resolutions were performed.

| Example | Structure | MS (M + 1) |
|---|---|---|
| 17 | 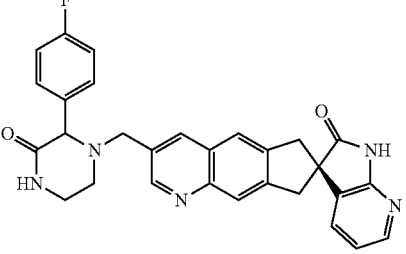 | 494 |

EXAMPLE 18

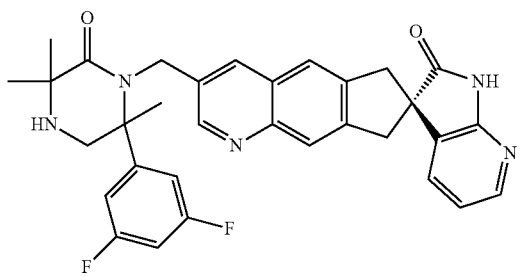 [SMILES: CC1(C)NCC(C)(c2cc(F)cc(F)c2)N(Cc2cnc3cc4c(cc3c2)C[C@@]2(C4)C(=O)Nc3ncccc32)C1=O]

(7S)-3-{[(2R)-2-(3,5-Difluorophenyl)-2,5,5-trimethyl-6-oxopiperazin-1-yl]methyl}-6,8-dihydrospiro[cyclopenta[g]quinoline-7,3'-pyrrolo[2,3-b]pyridin]-2'(1'H)-one, isomer B Step A. (±)-N-[2-[(tert-Butoxycarbonyl)amino]-2-(3,5-difluorophenyl)propyl]-2-methylalanine To a stirred solution of (±)-tert-butyl [1-(3,5-difluorophenyl)-1-methyl-2-oxoethyl]carbamate (4.00 g, 14.0 mmol, described in U.S. Patent Application Publication No. US 2007/0265225) and 2-methylalanine (4.34 g, 42.1 mmol) in AcOH (25 mL) was added sodium triacetoxyborohydride (3.57 g, 16.8 mmol). The reaction mixture was stirred for 24 h, with additional sodium triacetoxyborohydride (1.00 g) added at 16 and 20 h. The reaction mixture was diluted with water (75 mL) and extracted with $CH_2Cl_2$ (4×50 mL). The combined organic extracts were dried over $Na_2SO_4$, filtered, and concentrated in vacuo. The crude product was purified by silica gel chromatography, eluting with a gradient of $CH_2Cl_2$:MeOH:$NH_4OH$—97:3:1 to 85:15:1, to give the title compound. MS: m/z=373 (M+1).

Step B. (±)-N-[2-Amino-2-(3,5-difluorophenyl)propyl]-2-methylalanine

A solution of the (±)-N-[2-[(tert-butoxycarbonyl)amino]-2-(3,5-difluorophenyl)propyl]-2-methylalanine from Step A (878 mg, 2.36 mmol) in $CH_2Cl_2$ (9 mL) and $CF_3CO_2H$ (3 mL) was aged at ambient temperature for 3 h. The reaction mixture was concentrated in vacuo to give the title compound as the trifluoroacetate salt. MS: m/z=273 (M+1).

Step C. N-[2-(3,5-Difluorophenyl)-2-({[(7S)-2'-oxo-1', 2',6,8-tetrahydrospiro[cyclopenta[g]quinoline-7, 3'-pyrrolo[2,3-b]pyridin]-3-yl]methyl}amino)propyl]-2-methylalanine To a stirred solution of (7S)-2'-oxo-1',2',6,8-tetrahydrospiro[cyclopenta[g]quinoline-7,3'-pyrrolo[2,3-b]pyridine]-3-carbaldehyde (150 mg, 0.476 mmol, described in Intermediate 1), (±)-N—[2-amino-2-(3,5-difluorophenyl)propyl]-2-methylalanine trifluoroacetate from Step B (238 mg, 0.476 mmol), and AcOH (0.136 mL, 2.38 mmol) in DCE (3 mL) was added sodium triacetoxyborohydride (121 mg, 0.571 mmol). The reaction mixture was stirred for 4 d and then the solvent was removed in vacuo. The residue was dissolved in DMSO (5 mL) and purified by HPLC using a reversed phase C18 column and eluting with a gradient of $H_2O$:$CH_3CN$:$CF_3CO_2H$—90:10:0.1 to 5:95:0.1. The pure, product-containing fractions were combined and concentrated to give the title compound as the trifluoroacetate salt. MS: m/z=572 (M+1).

Step D. (7S)-3-{[(2R)-2-(3,5-Difluorophenyl)-2,5,5-trimethyl-6-oxopiperazin-1-yl]methyl}-6,8-dihydrospiro[cyclopenta[g]quinoline-7,3'-pyrrolo[2,3-b]pyridin]-2'(1'H)-one, isomer B A solution of N-[2-(3,5-difluorophenyl)-2-({[(7S)-2'-oxo-1',2',6,8-tetrahydrospiro[cyclopenta[g]quinoline-7,3'-pyrrolo[2,3-b]pyridin]-3-yl]methyl}amino)propyl]-2-methylalanine from Step D (150 mg, 0.262 mmol), EDC (60.4 mg, 0.315 mmol), HOBT (48.2 mg, 0.315 mmol), and DIEA (0.229 mL, 1.31 mmol) in DMF (5 mL) was stirred for 16 h. The reaction mixture was diluted with saturated aqueous $NaHCO_3$ (20 mL) and extracted with $CH_2Cl_2$ (3×10 mL). The combined organic extracts were dried over $Na_2SO_4$, filtered, and concentrated in vacuo. The crude product was purified by silica gel chromatography, eluting with a gradient of $CH_2Cl_2$:MeOH:$NH_4OH$—100:0:0 to 90:10:1, to give the title compound as a mixture of diastereomers. The mixture of diastereomers were resolved by HPLC, utilizing a Chiralpak AS-H column and eluting with MeOH:$CO_2$—20:80. The first major peak to elute was (7S)-3-{[(2R)-2-(3,5-Difluorophenyl)-2,5,5-trimethyl-6-oxopiperazin-1-yl]methyl}-6,8-dihydrospiro[cyclopenta[g]quinoline-7,3'-pyrrolo[2,3-b]pyridin]-2'(1'H)- one, isomer A, and the second major peak to elute was (7S)-{[(2R)-2-(3,5-Difluorophenyl)-2,5,5-trimethyl-6-oxopiperazin-1-yl]methyl}-6,8-dihydrospiro[cyclopenta[g]quinoline-7,3'-pyrrolo[2,3-b]pyridin]-2'(1'H)-one, isomer B, the title compound. MS: m/z=554 (M+1). HRMS: m/z=554.2365; calculated m/z=554.2362 for $C_{32}H_{30}F_2N_5O_2$.

EXAMPLE 19

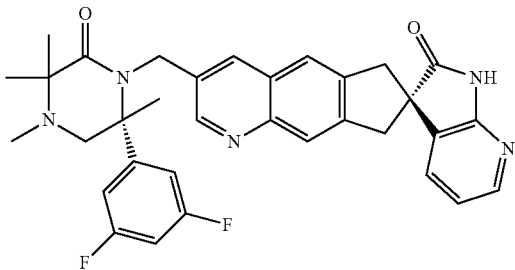 [SMILES: CN1C[C@@](C)(c2cc(F)cc(F)c2)N(Cc2cnc3cc4c(cc3c2)C[C@@]2(C4)C(=O)Nc3ncccc32)C(=O)C1(C)C]

(7S)-3-{[2-(3,5-Difluorophenyl)-2,4,5,5-tetramethyl-6-oxopiperazin-1-yl]methyl}-6,8-dihydrospiro[cyclopenta[g]quinoline-7,3'-pyrrolo[2,3-b]pyridin]-2'(1'H)-one, isomer B To a solution of (7S)-3-{[(2R)-2-(3,5-difluorophenyl)-2,5,5-trimethyl-6-oxopiperazin-1-yl]methyl}-6,8-dihydrospiro[cyclopenta[g]quinoline-7,3'-pyrrolo[2,3-b]pyridin]-2'(1'H)-one, isomer B (15 mg, 0.027 mmol, described in Example 18), paraformaldehyde (8.1 mg, 0.27 mmol), and AcOH (0.0078 mL, 0.14 mmol) in MeOH (1 mL) was added NaCNBH₃ (2.0 mg, 0.033 mmol). The reaction mixture was stirred for 16 h and then diluted with saturated aqueous NaHCO₃ (10 mL) and extracted with CH₂Cl₂ (3×10 mL). The combined organic extracts were dried over Na₂SO₄, filtered, and concentrated in vacuo. The crude product was dissolved in MeOH (1 mL). Sodium hydroxide (10 M, 0.014 mL, 0.14 mmol) and ethylenediamine (0.0037 mL, 0.054 mmol) were added and the solution was stirred for 30 min and then diluted with saturated aqueous NaHCO₃ (5 mL) and extracted with CH₂Cl₂ (3×5 mL). The combined organic extracts were dried over Na₂SO₄, filtered, and concentrated in vacuo. The crude product was purified by silica gel chromatography, eluting with a gradient of CH₂Cl₂:MeOH:NH₄OH—100:0:0 to 90:10:1, to give the title compound. MS: m/z=568 (M+1). HRMS: m/z=568.2520; calculated m/z=568.2519 for $C_{33}H_{32}F_2N_5O_2$.

Essentially following analogous procedures to those outlined for Example 18 the following example was prepared. The requisite starting materials were commercially available, described in the literature, or readily synthesized by one skilled in the art of organic synthesis. In some cases, straightforward protecting group strategies were applied, or chiral resolutions were performed.

| Example | Structure | MS (M + 1) |
|---------|-----------|------------|
| 20 | 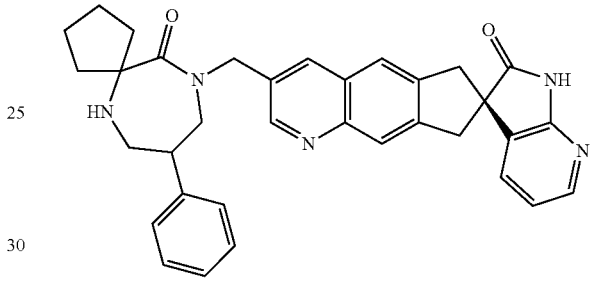 | 594 |

EXAMPLE 21

(7S)-3-[(11-Oxo-8-phenyl-6,10-diazaspiro[4.6]undec-10-yl)methyl]-6,8-dihydrospiro[cyclopenta[g]quinoline-7,3'-pyrrolo[2,3-b]pyridin]-2'(1'H)-one Step A. Methyl 3-[(tert-butoxycarbonyl)amino]-2-phenylpropanoate To a solution of Boc-3-amino-2-phenyl-propionic acid (2.0 g, 7.54 mmol) in methanol (10 mL) and chloroform (20 mL) was added (trimethylsilyl)diazomethane (5.65 mL, 2.0 M in diethyl ether) dropwise until the stirred solution became bright yellow. The solution was then stirred at ambient temperature for 30 minutes. The reaction was concentrated in vacuo to yield a residue, which was used without purification. MS: m/z=302 (M+Na).

Step B. tert-Butyl (3-oxo-2-phenylpropyl)carbamate

A solution of methyl 3-[(tert-butoxycarbonyl)amino]-2-phenylpropanoate from Step A (2.1 g, 7.52 mmol) in anhydrous dichloromethane (75 mL) was cooled to –78° C. under nitrogen and DIBAL-H (15 mL, 15 mmol, 1.0 M in hexanes) was added to the solution dropwise over 45 minutes. This solution was then stirred at –78° C. for 1 h. The reaction was then quenched by the addition of a saturated aqueous solution of Rochel's salt (75 mL) and the biphasic solution was stirred at ambient temperature for 30 minutes. The layers were separated and the aqueous layer was extracted twice with DCM. The combined organics were dried over sodium sulfate, filtered, and concentrated in vacuo to provide a residue. The residue was applied to a silica gel column for purification, eluting with a gradient of 1-3% methanol in DCM to yield the title compound. MS: m/z=250 (M+1).

Step C. Methyl 1-({3-[(tert-butoxycarbonyl)amino]-2-phenylpropyl}amino)cyclopentanecarboxylate Into a solution of tert-butyl (3-oxo-2-phenylpropyl)carbamate from Step B (0.5 g, 2 mmol) in dry chloroform (20 mL) was added methyl 1-amino-1-cyclopentanecarboxylate (0.431 g, 3.01 mmol). After 15 minutes, sodium triacetoxyborohydride (0.893 g, 4.21 mmol) was added. After 4 hours of stirring at ambient temperature, the reaction mixture was diluted with DCM and 5% sodium bicarbonate. The layers were separated and the aqueous layer was extracted once with DCM. The combined organics were dried over sodium sulfate, filtered, and concentrated in vacuo to yield a residue, which was subjected to a normal phase chromatography, eluting with a gradient of 1-6% methanol in DCM. Concentration of the fractions containing the product provided the title compound. MS: m/z=377 (M+1).

Step D. Methyl 1-[(3-amino-2-phenylpropyl)amino]cyclopentanecarboxylate

A solution of methyl 1-({3-[tert-butoxycarbonyl)amino]-2-phenylpropyl}amino)cyclopentanecarboxylate from Step C (0.53 g, 1.408 mmol) in ethyl acetate (14 mL) was cooled to 0° C. and anhydrous HCl gas was bubbled through the solution for 5 minutes. After 30 min, a stream of nitrogen was passed over the solution to remove some HCl. The reaction was then concentrated in vacuo to yield the title compound as a bis-HCl salt.

Step E. Methyl 1-{[3-({[(7S)-2'-oxo-1',2',6,8-tetrahydrospiro[cyclopenta[g]quinoline-7,3'-pyrrolo[2,3-b]pyridin]-3-yl]methyl}amino)-2-phenylpropyl]amino}cyclo-pentanecarboxylate To a stirred suspension of 2'-oxo-1',2', 6,8-tetrahydrospiro[cyclopenta[g]quinoline-7,3'-pyrrolo[2,3-b]pyridine]-3-carbaldehyde (80.0 mg, 0.254 mmol, Intermediate 1) and HOAc (31 µL, 0.533 mmol) in dry chloroform (3 mL) was added a solution of methyl 1-[(3-amino-2-phenylpropyl)amino]cyclopentanecarboxylate dihydrochloride from Step D (106 mg, 0.304 mmol) and Hunig's base (106 µL, 0.609 mmol) in dry chloroform (2 mL). After 15 minutes, sodium triacetoxyborohydride (108 mg, 0.507 mmol) was added. After 4 hours of stirring, the mixture was diluted with DCM and saturated aqueous sodium bicarbonate. The layers were separated and the aqueous layer was extracted once with DCM. The combined organics were dried over sodium sulfate, filtered, and concentrated in vacuo to provide a residue. The residue was then was applied to a silica gel column for purification, eluting with a gradient of DCM:MeOH (with 10% NH$_4$OH)—99:1 to 86:14 to give the title compound. MS: m/z=576 (M+1).

Step F. 1-{[3-({[(7S)-2'-Oxo-1',2',6,8-tetrahydrospiro[cyclopenta[g]quinoline-7,3'-pyrrolo[2,3-b]pyridin]-3-yl]methyl}amino)-2-phenylpropyl]amino}cyclo-pentanecarboxylic acid Into a solution of methyl 1-{[3-({[(7S)-2'-oxo-1',2',6,8-tetrahydrospiro[cyclopenta[g]quinoline-7,3'-pyrrolo[2,3-b]pyridin]-3-yl]methyl}amino)-2-phenylpropyl]amino}cyclopentanecarboxylate from Step E (0.136 g, 0.236 mmol) in methanol (2 mL) was added NaOH (0.472 mL, 1 M in water). The solution is then allowed to stir for 18 h at ambient temperature. Additional NaOH (0.472 mL, 1 M in water) was then added to the reaction, which was completed after another 24 h of stirring. The solution was then concentrated in vacuo and neutralized by addition of HCl (0.944 mL, 1 M in water). The resulting precipitate was filtered to yield the title compound. MS: m/z=562 (M+1).

Step G. (7S)-3-[(11-Oxo-8-phenyl-6,10-diazaspiro[4.6]undec-10-yl)methyl]-6,8-dihydrospiro[cyclopenta[g]quinoline-7,3'-pyrrolo[2,3-b]pyridin]-2'(1'H)-one To a solution of 1-{[3-({[(7,5)-2'-oxo-1',2',6,8-tetrahydrospiro[cyclopenta[g]quinoline-7,3'-pyrrolo[2,3-b]pyridin]-3-yl]methyl}amino)-2-phenylpropyl]amino}cyclopentanecarboxylic acid from Step F (30 mg, 0.053 mmol) and HOBt (8.2 mg, 0.053 mmol) in THF (1 mL) were added EDCI (13.3 mg, 0.069 mmol) and triethylamine (19 µL, 0.14 mmol). This solution was stirred at ambient temperature for 18 h. The solution was then concentrated to yield a residue, which was applied to a silica gel column for purification, eluting with a gradient of 1-7% methanol in DCM. Concentration of the fractions containing the product provided the title compound. MS: m/z=544 (M+1). HRMS: m/z=544.2708, calculated m/z=544.2707 for $C_{34}H_{34}N_5O_2$.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK—N-MC cell membranes was carried out essentially as described (Edvinsson et al. (2001) *Eur. J. Pharmacol.* 415, 39-44). Briefly, membranes (25 µg) were incubated in 1 mL of binding buffer [10 mM HEPES, pH 7.4, 5 mM MgCl$_2$ and 0.2% bovine serum albumin (BSA)] containing 10 pM $^{125}$I-CGRP and antagonist. After incubation at room temperature for 3 h, the assay was terminated by filtration through GFB glass fibre filter plates (PerkinElmer) that had been blocked with 0.5% polyethyleneimine for 3 h. The filters were washed three times with ice-cold assay buffer (10 mM HEPES, pH 7.4 and 5 mM MgCl$_2$), then the plates were air dried. Scintillation fluid (50 µL) was added and the radioactivity was counted on a Topcount (Packard Instrument). Data analysis was carried out by using Prism and the K$_i$ was determined by using the Cheng-Prusoff equation (Cheng & Prusoff (1973) *Biochem. Pharmacol.* 22, 3099-3108).

RECOMBINANT RECEPTOR: Human CL receptor (Genbank accession number L76380) was subcloned into the expression vector pIREShyg2 (BD Biosciences Clontech) as a 5'NheI and 3'PmeI fragment. Human RAMP1 (Genbank accession number AJ001014) was subcloned into the expression vector pIRESpuro2 (BD Biosciences Clontech) as a 5'NheI and 3'NotI fragment. HEK 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 µg/mL streptomycin, and maintained at 37° C. and 95% humidity. Cells were subcultured by treatment with 0.25% trypsin with 0.1% EDTA in HBSS. Stable cell line generation was accomplished by co-transfecting 10 µg of DNA with 30 µg Lipofectamine 2000 (Invitrogen) in 75 cm$^2$ flasks. CL receptor and RAMP1 expression constructs were co-transfected in equal amounts. Twenty-four hours after transfection the cells were diluted and selective medium (growth medium+300 µg/mL hygromycin and 1 µg/mL puromycin) was added the following day. A clonal cell line was generated by single cell deposition utilizing a FACS Vantage SE (Becton Dickinson). Growth medium was adjusted to 150 µg/mL hygromycin and 0.5 µg/mL puromycin for cell propagation.

RECOMBINANT RECEPTOR BINDING ASSAY: Cells expressing recombinant human CL receptor/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 20 µg of membranes were incubated in 1 ml binding buffer (10 mM HEPES, pH 7.4, 5 mM $MgCl_2$, and 0.2% BSA) for 3 hours at room temperature containing 10 µM $^{125}$I-hCGRP (GE Healthcare) and antagonist. The assay was terminated by filtration through 96-well GFB glass fiber filter plates (PerkinElmer) that had been blocked with 0.05% polyethyleneimine. The filters were washed 3 times with ice-cold assay buffer (10 mM HEPES, pH 7.4 and 5 mM $MgCl_2$). Scintillation fluid was added and the plates were counted on a Topcount (Packard). Non-specific binding was determined and the data analysis was carried out with the apparent dissociation constant ($K_i$) determined by using a non-linear least squares fitting the bound CPM data to the equation below:

$$Y_{obsd} = \frac{Y_{min} + (Y_{max} - Y_{min})(100 - \% I_{max}/100) + (Y_{max} - Y_{min})(\% I_{max} - \% I_{min}/100) +}{1 + ([Drug]/K_i(1 + [Radiolabel]/K_d)^{nH}}$$

Where Y is observed CPM bound, $Y_{max}$ is total bound counts, $Y_{min}$ is non specific bound counts, ($Y_{max}-Y_{min}$) is specific bound counts, % $I_{max}$ is the maximum percent inhibition, % I min is the minimum percent inhibition, radiolabel is the probe, and the $K_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 mM at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 µM and incubated for 30 min at 37° C. Human α-CGRP was added to the cells at a concentration of 0.3 nM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; GE Healthcare). Dose response curves were plotted and $IC_{50}$ values determined from a 4-parameter logistic fit as defined by the equation $y=((a-d)/(1+(x/c)^b)+d$, where y=response, x=dose, a=max response, d=min response, c=inflection point and b=slope.

The compounds of the invention were tested according to the foregoing recombinant receptor binding assay, and typically had activity as antagonists of the CGRP receptor in the aforementioned assays, with a $K_i$ value of less than 5 µM.

Exemplary $K_i$ values in the recombinant receptor binding assay for exemplary compounds of the invention are provided in the table below:

| Example | Ki (nM) |
|---|---|
| 5 | 0.057 |
| 6 | 0.34 |
| 8 | 0.14 |
| 9 | 0.77 |
| 10 | 1.3 |
| 12 | 0.28 |
| 13 | 0.062 |
| 15 | 0.49 |
| 16 | 0.89 |
| 17 | 57 |

The following abbreviations are used throughout the text:
Me: methyl
Et: ethyl
t-Bu: tert-butyl
Ar: aryl
Ph: phenyl
Bn: benzyl
Ac: acetate
BOC: t-butyloxycarbonyl
BOP: Benzotriazole-1-yl-oxy-tris-(dimethylamino)-phosphonium hexafluorophosphate
DIEA: N,N-Diisopropyl-ethylamine
HOBT: 1-Hydroxybenzotriazole
HOAT: 1-Hydroxy-7-Azabenzotriazole
EDC: 1-Ethyl-3-(3-dimethylaminopropyl)carbodiimide
DCM: dichloromethane
DCE: dichloroethane
EDCI: 1-Ethyl-3-(3'-dimethylaminopropyl)carbodiimide hydrochloride
HATU: 2-(1H-7-Azabenzotriazol-1-yl)-1,1,3,3-tetramethyl uronium hexafluorophosphate Methanaminium
PyCIU: 1-(Chloro-1-pyrrolidinylmethylene)pyrrolidiniumhexafluorophosphate
TMS: trimethylsilyl
TsOH: p-toluene sulfonic acid
TFA: Trifluoroacetic acid
Dba: dibenzylideneacetone
DiPEA: Diisopropylethylamine
EDTA: Ethylenediaminetetracetic acid
DAST: diethylaminsulfur trifluoride
BINAP: 2,2'-bis(diphenylphosphino)-11'-binaphthyl
DMF: dimethylformamide
HMDS: hexamethyldisilazane
THF: tetrahydrofuran
Ac: acetyl or acetate
DMSO: dimethylsulfoxide
DMEM: Dulbecco's Modified Eagle Medium (High Glucose)
FBS: fetal bovine serum
BSA: bovine serum albumin
PBS: phosphate-buffered saline
HEPES: N-(2-Hydroxyethyl)piperazine-N'-2-ethanesulfonic Acid
rt: room temperature
d: days
h: hours
aq: aqueous
HPLC: high performance liquid chromatography
LCMS: liquid chromatography-mass spectrometry While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of Formula I:

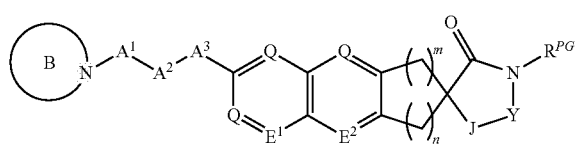

(I)

wherein:

$E^1$ and $E^2$ are each independently selected from the group consisting of:
  (1) =N—,
  (2) =N$^+$(O$^-$)—, and
  (3) =C(R$^5$)—
wherein at least one of $E^1$ and $E^2$ must contain nitrogen;

each Q is =C(R$^5$)—;

$A^1$, $A^2$ and $A^3$ are each independently selected from the group consisting of:
  (1) a bond,
  (2) —CR$^1$R$^2$—,
  (3) —NR$^b$—,
  (4) —CR$^1$R$^2$—NR$^b$—,
  (5) —CR$^1$R$^2$—CH$_2$—,
  (6) —O—CR$^1$R$^2$—,
  (7) —CR$^1$R$^2$—O—, and
  (8) —C(=O)—,
    provided that at least one of $A^1$, $A^2$ and $A^3$ is not a bond;

$R^1$ and $R^2$ are each independently selected from the group consisting of:
  (1) hydrogen,
  (2) C$_{1-6}$ alkyl, which is unsubstituted or substituted with 1-5 substituents each independently selected from the group consisting of:
    (a) —C$_{3-6}$cycloalkyl, which is unsubstituted or substituted with 1-5 halo,
    (b) —OR$^a$,
    (c) halo, and
    (d) phenyl, which is unsubstituted or substituted with 1-5 halo,
  (3) —OR$^a$,
  (4) halo, and
  (5) phenyl or pyridinyl, which is unsubstituted or substituted with 1-5 substituents each independently selected from the group consisting of:
    (a) halo,
    (b) —OR$^a$,
    (c) —CN, and
    (d) —C$_{1-6}$alkyl, which is unsubstituted or substituted with 1-5 halo;

$R^5$ is selected from the group consisting of:
  (1) hydrogen
  (2) —C$_{1-6}$alkyl, which is unsubstituted or substituted with 1-6 halo,
  (3) halo,
  (4) —OR$^a$, and
  (5) —CN;

B is a heterocycle selected from the group consisting of:

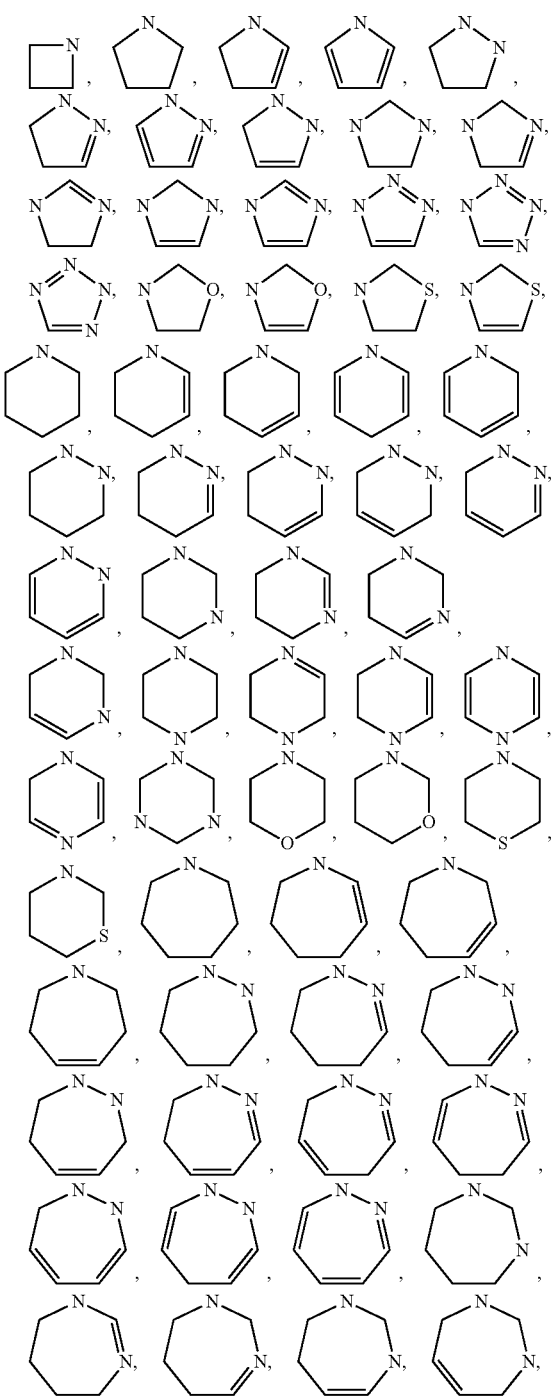

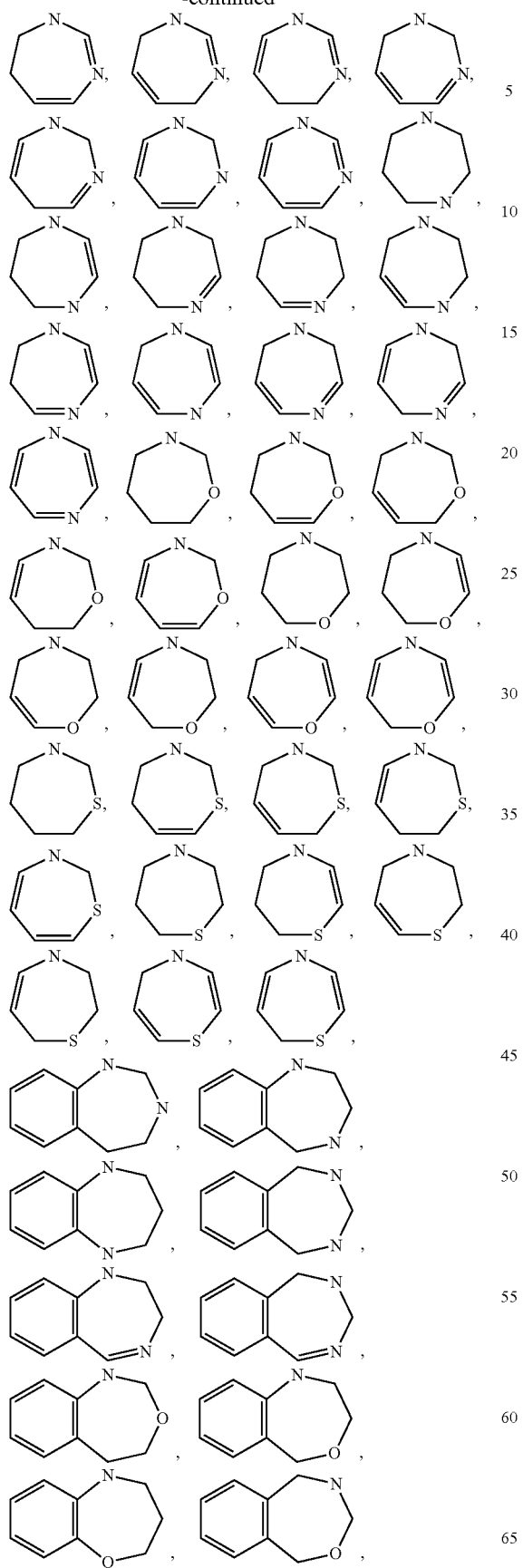
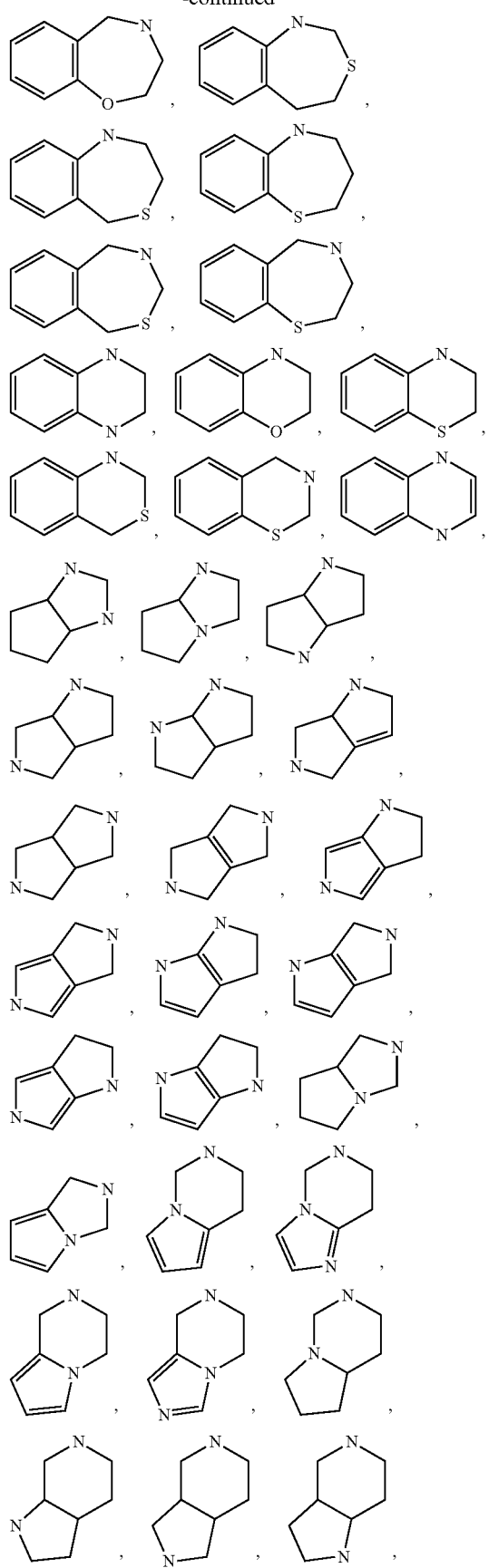

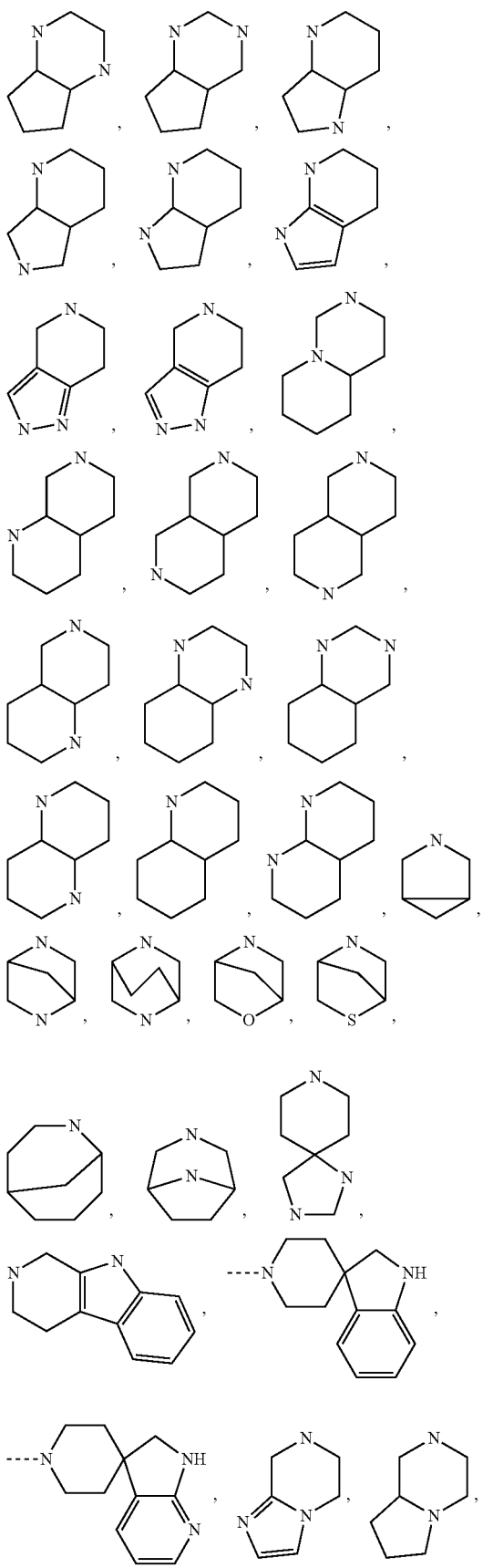

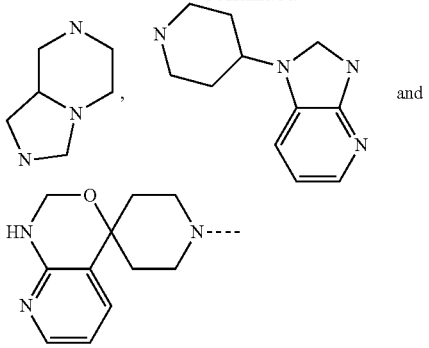

where B is linked to A¹ via a nitrogen atom in B and
where B is unsubstituted or substituted with 1-6 substitutents independently selected from the group consisting of $R^3$, $R^4$, $R^6$, $R^7$, $R^8$ and $R^9$;

$R^3$, $R^4$, $R^6$, $R^7$, $R^8$ and $R^9$ are each independently selected from the group consisting of:

(1) hydrogen,
(2) —$C_{1-6}$alkyl, which is unsubstituted or substituted with 1-5 substituents each independently selected from the group consisting of:
 (a) halo,
 (b) —OR$^a$,
 (c) —$C_{3-6}$cycloalkyl,
 (d) phenyl or heterocycle, wherein said heterocycle is selected from the group consisting of: benzodioxolyl, imidazolyl, indolyl, pyridyl, pyrimidinyl, pyrazinyl, pyridazinyl, piperdinyl, piperazinyl, pyrrolidinyl, thienyl, morpholinyl, thiazolyl and oxazolyl, which phenyl or heterocycle is unsubstituted or substituted with 1-5 substituents each independently selected from the group consisting of:
  (i) halo,
  (ii) —$C_{1-6}$alkyl, which is unsubstituted or substituted with 1-5 halo, and
  (iii) —OR$^a$,
 (e) —$CO_2R^a$,
 (f) —C(=O)NR$^b$R$^c$,
 (g) —S(O)$_r$R$^d$,
 (h) —CN,
 (i) —NR$^b$R$^a$,
 (j) —N(R$^b$)C(=O)R$^a$,
 (k) —N(R$^b$)SO$_2$R$^d$,
 (l) —CF$_3$,
 (m) —O—CO$_2$R$^d$,
 (n) —O—(C=O)—NR$^b$R$^c$,
 (o) —NR$^b$—(C=O)—NR$^b$R$^c$, and
 (p) —C(=O)R$^a$,
(3) —$C_{3-6}$cycloalkyl, which is unsubstituted or substituted with 1-5 substituents each independently selected from the group consisting of:
 (a) halo,
 (b) —CN,
 (c) —$C_{1-6}$alkyl, which is unsubstituted or substituted with 1-5 halo,
 (d) —OR$^a$,and
 (e) phenyl, which is unsubstituted or substituted with 1-5 substituents each independently selected from the group consisting of:
  (i) —OR$^a$,
  (ii) halo,
  (iii) —CN, and (iv) —$C_{1-6}$alkyl, which is unsubstituted or substituted with 1-5 halo,
(4) phenyl or heterocycle, wherein said heterocycle is selected from: benzimidazolyl, benzoxazinyl, benzoxazolyl, indanyl, indolyl, morpholinyl, oxadiazolyl, oxazolyl, pyridyl, pyrimidinyl, pyrazinyl, pyrazolyl, pyridazinyl, piperdinyl, piperazinyl, pyrrolidinyl, thienyl, tetrazolyl, thiazolyl, and triazolyl, which phenyl or heterocycle is unsubstituted or substituted with 1-5 substituents each independently selected from the group consisting of:
  (a) halo,
  (b) OR$^a$,
  (c) —$C_{3-6}$cycloalkyl,
(d) phenyl or pyridyl, which is unsubstituted or substituted with 1-5 substituents each independently selected from the group consisting of:
  (i) halo,
  (ii) $C_{1-6}$alkyl, which is unsubstituted or substituted with 1-6 halo, and
  (iii) —OR$^a$,
(e) —CO$_2$R$^a$,
(f) —C(=O)NR$^b$R$^c$,
(g) —S(O)$_v$R$^d$,
(h) —CN,
(i) —NR$^b$R$^c$,
(j) —N(R$^b$)C(=O)R$^a$,
(k) —N(R$^b$)SO$_2$R$^d$,
(l) —O—CO$_2$R$^d$,
(m) —O—(C=O)—NR$^b$R$^c$,
(n) —NR$^b$—(C=O)—NR$^b$R$^c$,
(o) oxo,
(p) —C(=O)R$^a$, and
(q) —$C_{1-6}$alkyl, which is unsubstituted or substituted with 1-6 halo,
(5) halo,
(6) oxo,
(7) —OR$^a$,
(8) —CN,
(9) —CO$_2$R$^a$,
(10) —C(=O)R$^a$,
(11) —NR$^b$R$^c$,
(12) —S(O)$_v$R$^d$,
(13) —C(=O)NR$^b$R$^c$,
(14) —O—(C=O)R$^a$,
(15) —O—CO$_2$R$^d$,
(16) —N(R$^b$)CO$_2$R$^d$,
(17) —O—(C=O)—NR$^b$R$^c$,
(18) —NR$^b$—(C=O)—NR$^b$R$^c$,
(19) —SO$_2$NR$^b$R$^c$, and
(20) —N(R$^b$)SO$_2$R$^d$,
or R$^7$ and R$^8$ and the atom(s) to which they are attached join to form a ring selected from the group consisting of azetidinyl, aziridinyl, cyclobutyl, cycloheptyl, cyclohexyl, cyclooctyl, cyclopentyl, cyclopropyl, dihydrobenzofuranyl, dihydrobenzopyranyl, dioxanyl, dioxoalanyl, indanyl, indenyl, indolinyl, isoindolinyl, morpholinyl, oxetanyl, piperazinyl, piperidinyl, pyrrolidinyl, tetrahydrofuranyl, tetrahydroisoquinolinyl, tetrahydronaphthyl, tetrahydroquinolinyl, tetrahydropyranyl, tetrahydrothiapyranyl, tetrahydrothienyl, thiamorpholinyl, and thietanyl, wherein the sulfur is optionally oxidized to the sulfone or sulfoxide, which ring is unsubstituted or substituted with 1-5 substituents each independently selected from the group consisting of:
  (a) —$C_{1-6}$alkyl, which is unsubstituted or substituted with 1-3 substituents each independently selected from the group consisting of:
    (i) halo,
    (ii) —OR$^a$,
    (iii) —$C_{3-6}$cycloalkyl,
    (iv) —CO$_2$R$^a$,
    (v) —NR$^b$R$^c$,
    (vi) —S(O)$_v$R$^d$,
    (vii) —C(=O)NR$^b$R$^c$, and
    (viii) phenyl, which is unsubstituted or substituted with 1-5 halo,
  (b) phenyl or heterocycle, wherein heterocycle is selected from the group consisting of: pyridyl, pyrimidinyl, pyrazinyl, pyridazinyl, piperdinyl, piperazinyl, pyrrolidinyl, thienyl, morpholinyl, thiazolyl and oxazolyl, wherein the phenyl or heterocycle is optionally fused to the ring, and which phenyl or heterocycle is unsubstituted or substituted with 1-5 substituents each independently selected from:
    (i) halo,
    (ii) —$C_{1-6}$alkyl, which is unsubstituted or substituted with 1-5 halo, and
    (iii) —OR$^a$,
  (c) —OR$^a$,
  (d) halo,
  (e) —CO$_2$R$^a$,
  (f) —C(=O)NR$^b$R$^c$,
  (g) —S(O)$_v$R$^d$,
  (h) —CN,
  (i) —NR$^b$R$^c$,
  (j) —N(R$^b$)C(=O)R$^a$,
  (k) —N(R$^b$)SO$_2$R$^d$,
  (l) —O—(C=O)R$^a$,
  (m) —O—CO$_2$R$^d$,
  (n) —O—(C=O)—NR$^b$R$^c$,
  (o) —NR$^b$—(C=O)—NR$^b$R$^c$,
  (p) —C(=O)R$^a$, and
  (q) oxo;
R$^{PG}$ is independently selected from the group consisting of:
  (1) hydrogen,
  (2) —$C_{1-6}$alkyl which is unsubstituted or substituted with 1-5 halo,
  (3) —CH$_2$OR$^a$,
  (4) —CH$_2$—O—CH$_2$CH$_2$Si(CH$_3$)$_3$,
  (5) —(CH$_2$)$_k$-phenyl, which is unsubstituted or substituted with 1-3 substituents each independently selected from the group consisting of:
    (a) halo,
    (b) —OR$^a$,
    (c) —CN, and
    (d) —$C_{1-6}$alkyl, which is unsubstituted or substituted with 1-6 halo;
J is
Y is
R$^{16a}$ and R$^{16b}$ and the atom(s) to which they are attached join to form a pyridyl ring which ring is unsubstituted or substituted with 1-5 substituents each independently selected from the group consisting of:
  (a) —$C_{1-6}$allcyl, which is unsubstituted or substituted with 1-3 substituents each independently selected from the group consisting of:
    (i) halo,
    (ii) —OR$^a$,
    (iii) —$C_{3-6}$cycloalkyl, (iv) phenyl or heterocycle, wherein heterocycle is selected from pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from the group consisting of:
(I) —OR$^a$,
(II) halo,
(III) —CN, and
(IV) —C$_{1-6}$alkyl which is unsubstituted or substituted with 1-6 halo,
(v) —CO$_2$R$^a$,
(vi) —NR$^b$R$^c$,
(vii) —S(O)$_v$R$^d$,
(viii) —C(=O)NR$^b$R$^c$,
(ix) —N(R$^b$)CO$_2$R$^a$, and
(x) —N(R$^b$)SO$_2$R$^d$,
(b) phenyl or heterocycle, wherein said heterocycle is selected from pyridyl, pyrimidinyl, pyrazinyl, pyridazinyl, piperidinyl, azetidinyl, piperazinyl, pyrrolidinyl, thienyl and morpholinyl, which phenyl or heterocycle is unsubstituted or substituted with 1-5 substituents each independently selected from the group consisting of:
(i) halo,
(ii) —OR$^a$,
(iii) —CN, and
(iv) —C$_{1-6}$alkyl which is unsubstituted or substituted with 1-6 halo,
(c) halo,
(d) —S(O)$_v$R$^d$,
(e) —OR$^a$,
(f) —CN,
(g) —C(=O)R$^a$,
(h) —NR$^b$R$^c$,
(i) —C(=O)NR$^b$R$^c$,
(j) —CO$_2$R$^a$,
(k) —(NR$^b$)CO$_2$R$^a$,
(l) —O—(C=O)—NR$^b$R$^c$,
(m) —(NR$^b$)—(C=O)—NR$^b$R$^c$,
(n) oxo, and
(o) —(NR$^b$)SO$_2$R$^d$;
R$^a$ is selected from the group consisting of:
(1) hydrogen,
(2) C$_{1-6}$alkyl, which is unsubstituted or substituted with 1-7 substituents each independently selected from the group consisting of:
(a) halo,
(b) —O—C$_{1-6}$alkyl, which is unsubstituted or substituted with 1-6 halo,
(c) hydroxyl,
(d) —C(=O)—O—C$_{1-6}$alkyl, which is unsubstituted or substituted with 1-6 halo,
(e) —CN, and
(f) phenyl or heterocycle wherein said heterocycle is selected from the group consisting of pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from the group consisting of:
(i) halo,
(ii) —O—C$_{1-6}$alkyl, which is unsubstituted or substituted with 1-6 halo,
(iii) —CN,
(iv) nitro,
(v) hydroxyl, and
(vi) —C$_{1-6}$allcyl, which is unsubstituted or substituted with 1-6 halo,
(3) phenyl or heterocycle wherein said heterocycle is selected from pyridyl, indolyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from the group consisting of:
(a) halo,
(b) —CN,
(c) —O—C$_{1-6}$allcyl, which is unsubstituted or substituted with 1-6 halo,
(d) nitro,
(e) hydroxyl, and
(f) —C$_{1-6}$alkyl, which is unsubstituted or substituted with 1-6 halo, and
(4) —C$_{3-6}$cycloalkyl, which is unsubstituted or substituted with 1-6 halo;
R$^b$ and R$^c$ are each independently selected from the group consisting of:
(1) hydrogen,
(2) C$_{1-6}$alkyl, which is unsubstituted or substituted with 1-7 substituents each independently selected from the group consisting of:
(a) halo,
(b) —OR$^a$,
(c) —CN,
(d) —CO$_2$R$^a$,
(e) phenyl or heterocycle, wherein said heterocycle is selected from the group consisting of pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from the group consisting of:
(i) halo,
(ii) —OR$^a$,
(iii) —C$_{1-6}$alkyl, which is unsubstituted or substituted with 1-6 halo, and
(iv) nitro,
(3) phenyl or heterocycle wherein said heterocycle is selected from the group consisting of pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from the group consisting of:
(a) halo,
(b) —OR$^a$,
(c) —C$_{1-6}$alkyl, which is unsubstituted or substituted with 1-6 halo,
(d) —C$_{3-6}$cycloalkyl, which is unsubstituted or substituted with 1-6 halo,
(e) —CN, and
(f) —CO$_2$R$^a$,
(4) —C$_{3-6}$cycloalkyl, which is unsubstituted or substituted with 1-6 halo;
or R$^b$ and R$^c$ and the nitrogen to which they are attached join to form a 4-, 5-, or 6-membered ring optionally containing an additional heteroatom selected from N, O and S, wherein the sulfur is optionally oxidized to the sulfone or sulfoxide, which ring is unsubstituted or substituted with 1-4 substituents each independently selected from the group consisting of:
(a) halo,
(b) —OR$^a$, and
(c) —C$_{1-6}$alkyl, which is unsubstituted or substituted with 1-6 halo, and
(d) phenyl;

R$^d$ is selected from the group consisting of:
(1) C$_{1-6}$alkyl, which is unsubstituted or substituted with 1-7 substituents each independently selected from the group consisting of:
(a) halo,
(b) —OR$^a$,
(c) —CO$_2$R$^a$
(d) —CN, and
(e) phenyl or heterocycle wherein said heterocycle is selected from the group consisting of pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from the group consisting of:
(i) halo,
(ii) —OR$^a$,
(iii) —CN,
(iv) nitro, and
(v) —C$_{1-6}$alkyl, which is unsubstituted or substituted with 1-6 halo,
(2) phenyl or heterocycle wherein said heterocycle is selected from the group consisting of pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from the group consisting of:
(a) halo,
(b) —OR$^a$,
(c) —C$_{1-6}$alkyl, which is unsubstituted or substituted with 1-6 halo,
(d) —C$_{3-6}$cycloalkyl, which is unsubstituted or substituted with 1-6 halo
(e) nitro,
(f) —CN, and
(g) —CO$_2$R$^a$,
(3) —C$_{3-6}$cycloalkyl, which is unsubstituted or substituted with 1-6 halo;

m is 1;
n is 1;
v is 0, 1, or 2;
k is 0, 1, or 2;
or a pharmaceutically acceptable salt thereof and tautomers thereof and individual enantiomers and diastereomers thereof.

2. A compound of claim 1, or a pharmaceutically acceptable salt thereof, wherein A$^2$ and A$^3$ are each a bond, and A$^1$ is selected from the group consisting of:
(1)—CR$^1$R$^2$—,
(2)—NR$^b$—,
(3)—CR$^1$R$^2$—NR$^b$—,
(4)—CR$^1$R$^2$—CH$_2$—,
(5)—O—CR$^1$R$^2$—,
(6)—CR$^1$R$^2$—O—, and
(7)—C(=O)—.

3. A compound of claim 1, or a pharmaceutically acceptable salt thereof, wherein B is selected from the group consisting of:

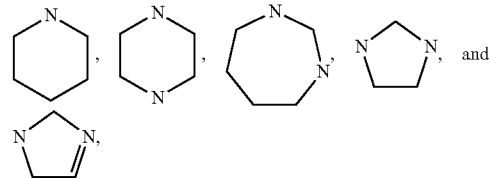

wherein B is unsubstituted or substituted with 1-6 substitutents independently selected from the group consisting of R$^3$, R$^4$, R$^6$, R$^7$, R$^8$ and R$^9$, and
R$^3$, R$^4$, R$^6$, R$^7$, R$^8$ and R$^9$ are each independently selected from the group consisting of:
(1) hydrogen,
(2) —C$_{1-6}$alkyl, which is unsubstituted or substituted with 1-5 substituents each independently selected from the group consisting of:
(a) halo,
(b) —OR$^a$,
(c) —C$_{3-6}$cycloalkyl,
(d) phenyl, which phenyl is unsubstituted or substituted with 1-5 halogen,
(3) —C$_{3-6}$cycloalkyl, which is unsubstituted or substituted with 1-5 substituents each independently selected from the group consisting of:
(a) halo,
(b) —CN,
(c) —C$_{1-6}$alkyl, which is unsubstituted or substituted with 1-5 halo,
(d) —OR$^a$, and
(e) phenyl, which is unsubstituted or substituted with 1-5 substituents each independently selected from the group consisting of:
(i)—OR$^a$,
(ii) halo,
(iii) —CN, and
(iv)—C$_{1-6}$alkyl, which is unsubstituted or substituted with 1-5 halo,
(4) phenyl, which is unsubstituted or substituted with 1-5 halogen, and
(5) oxo,
or R$^7$ and R$^8$ and the atom(s) to which they are attached join to form a ring selected from the group consisting of cycloheptyl, cyclohexyl, cyclooctyl, cyclopentyl or tetrahydronaphthyl, which ring is unsubstituted or substituted with 1-5 substituents each independently selected from the group consisting of:
(a) —C$_{1-6}$alkyl, which is unsubstituted or substituted with 1-3 substituents each independently selected from halo,
(b) phenyl, wherein the phenyl is optionally fused to the ring, and which phenyl or heterocycle is unsubstituted or substituted with 1-5 substituents each independently selected from the group consisting of:
(i) halo,
(ii) —C$_{1-6}$alkyl, which is unsubstituted or substituted with 1-5 halo, and
(iii) —OR$^a$.

4. A compound of claim 1, or a pharmaceutically acceptable salt thereof, wherein B is selected from the group consisting of:

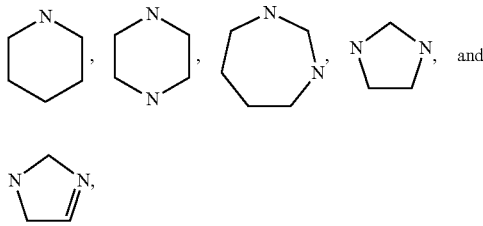

wherein B is unsubstituted or substituted with 1-6 substitutents independently selected from the group consisting of $R^3$, $R^4$, $R^6$, $R^7$, $R^8$ and $R^9$, or $R^7$ and $R^8$ and the atom(s) to which they are attached join to form a ring selected from the group consisting of cycloheptyl, cyclohexyl, cyclopentyl, and tetrahydronaphthyl.

5. A compound of claim 1, or a pharmaceutically acceptable salt thereof, wherein B is selected from the group consisting of:

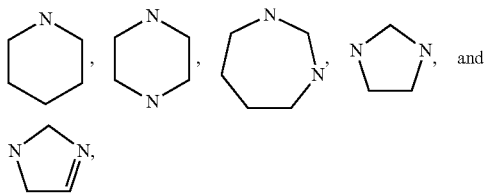

wherein B is substituted with 1-6 substitutents independently selected from the group consisting of $R^3$, $R^4$, $R^6$, $R^7$, $R^8$ and $R^9$, and at least one of $R^3$, $R^4$, $R^6$, $R^7$, $R^8$ and $R^9$ is oxo.

6. A compound of claim 1, or a pharmaceutically acceptable salt thereof, wherein B is selected from the group consisting of:

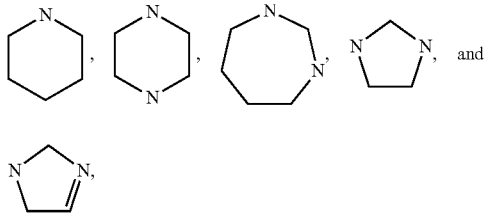

wherein B is unsubstituted or substituted with 1-6 substitutents independently selected from the group consisting of $R^3$, $R^4$, $R^6$, $R^7$, $R^8$ and $R^9$, and at least one of $R^3$, $R^4$, $R^6$, $R^7$, $R^8$ and $R^9$ is phenyl, optionally substituted with one or two halo.

7. A compound of claim 1, or a pharmaceutically acceptable salt thereof, wherein $E^1$ is nitrogen and $E^2$ is =$C(R^5)$—.

8. A compound of claim 1, or a pharmaceutically acceptable salt thereof, wherein $E^2$ is nitrogen and $E^1$ is =C(R5)—.

9. A compound of claim 1, or a pharmaceutically acceptable salt thereof, which is a compound of formula (II)

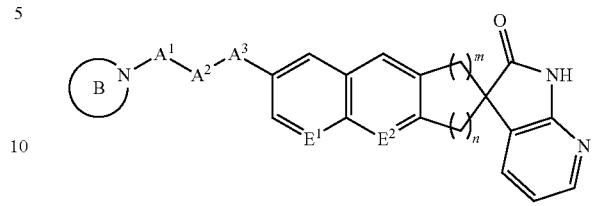

or a pharmaceutically acceptable salt thereof and tautomers thereof and individual enantiomers and diastereomers thereof.

10. A compound of claim 9, or a pharmaceutically acceptable salt thereof, wherein $A^2$ and $A^3$ are each a bond, and $A^1$ is selected from the group consisting of:

(1) —$CR^1R^2$—, (2) —$NR^b$—, (3) —$CR^1R^2$—$NR^b$—, (4) —$CR^1R^2$—$CH_2$—, (5) —O—$CR^1R^2$—, (6) —$CR^1R^2$—O—, and (7) —C(=O)—.

11. A compound of claim 10, or a pharmaceutically acceptable salt thereof, wherein B is selected from the group consisting of:

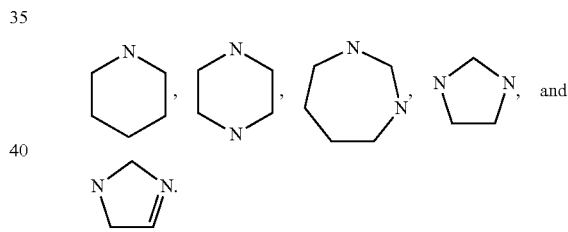

12. A compound of claim 11, or a pharmaceutically acceptable salt thereof, wherein $E^1$ is nitrogen and $E^2$ is =$C(R^5)$—.

13. A compound of claim 9, or a pharmaceutically acceptable salt thereof, wherein $E^2$ is nitrogen and $E^1$ is =$C(R^5)$—.

14. A compound of claim 1, or a pharmaceutically acceptable salt thereof, which is a compound of formula (III)

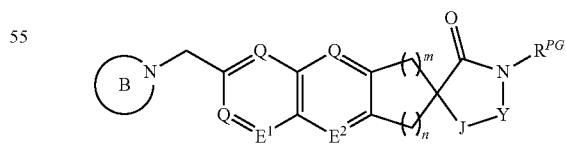

or a pharmaceutically acceptable salt thereof and tautomers thereof and individual enantiomers and diastereomers thereof.

15. A compound of claim 14, or a pharmaceutically acceptable salt thereof, wherein B is selected from the group consisting of:

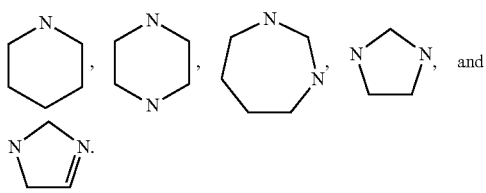

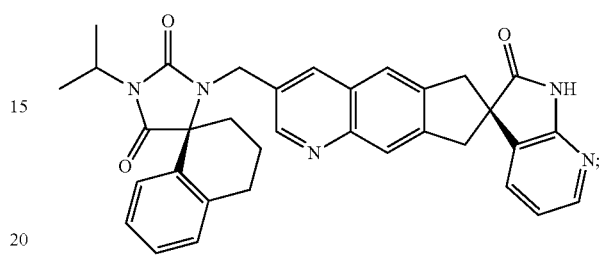

16. A compound of claim 1, which is a compound of formula (IV)

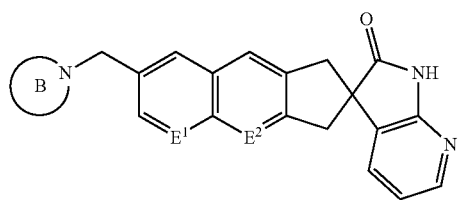

or a pharmaceutically acceptable salt thereof and tautomers thereof and individual enantiomers and diastereomers thereof.

17. A compound of claim 1, which is selected from the group consisting of

- (7S)-3-{[(6S)-6-(3,5-Difluorophenyl)-3,3-dimethyl-2-oxopiperidin-1-yl]methyl}-6,8-dihydrospiro[cyclopenta[g]quinoline-7,3'-pyrrolo[2,3 -b]pyridin]-2'(1'H)-one;
- (7 S)-3 -{[(3R)-3 -(3 ,5-Difluorophenyl)-3-methyl-5-oxo-1,4-diazaspiro[5.6]dodec-4-yl]methyl}-6,8-dihydrospiro[cyclopenta[g]quinoline-7,3'-pyrrolo[2,3-b]pyridin]-2'(1'H)-one;
- (7S)-3-{[(9S)-11-Oxo-9-phenyl-6,10-diazaspiro[4.6]undec-10-yl]methyl}-6,8-dihydrospiro[cyclopenta[g]quinoline-7,3'-pyrrolo[2,3-b]pyridin]-2'(1'H)-one;
- (7S)-3-[(2-Phenylpiperidin-1-yl)methyl]-6,8-dihydrospiro [cyclopenta[g]quinoline-7,3'-pyrrolo[2,3 -b]pyridin]-2'(1'H)-one;
- (7S)-3-{[(2R)-2-(3,5-Difluorophenyl)-2,5,5-trimethyl-6-oxopiperazin-1-yl]methyl}-6,8-dihydrospiro[cyclopenta[g]quinoline-7,3'-pyrrolo[2,3-b]pyridin]-2'(1'H)-one, isomer B;
- (7S)-3-{[2-(3,5-Difluorophenyl)-2,4,5,5-tetramethyl-6-oxopiperazin-1-yl]methyl}-6,8-dihydrospiro[cyclopenta[g]quinoline-7,3'-pyrrolo[2,3-b]pyridin]-2'(1'H)-one, isomer B;
- (7S)-3-[(11-Oxo-8-phenyl-6,10-diazaspiro[4.6]undec-10-yl)methyl]-6,8-dihydrospiro [cyclopenta[g]quinoline-7,3'-pyrrolo[2,3 -b]pyridin]-2'(1'H)-one;

or a pharmaceutically acceptable salt thereof.

18. A compound of claim 1, which is selected from the group consisting of

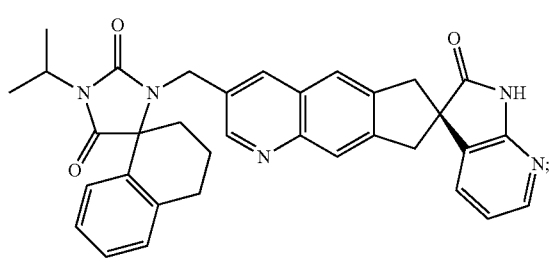

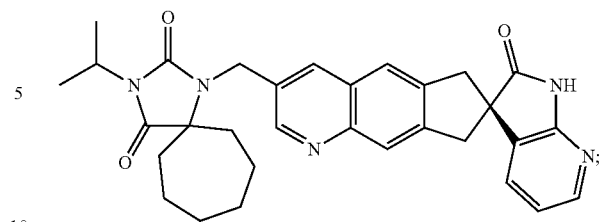

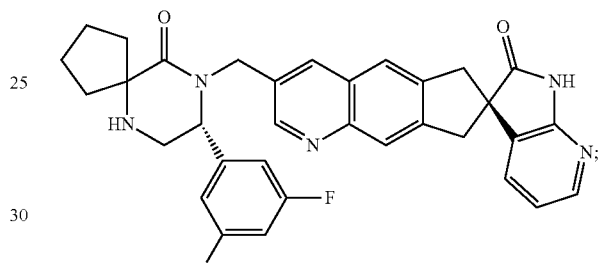

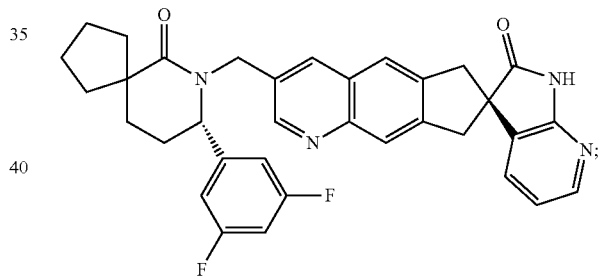

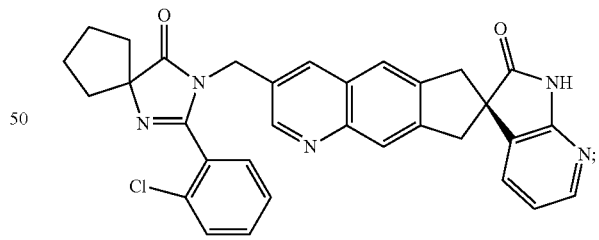

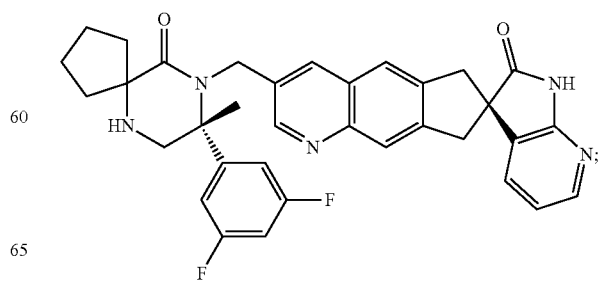

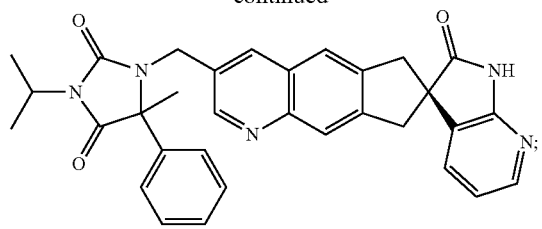

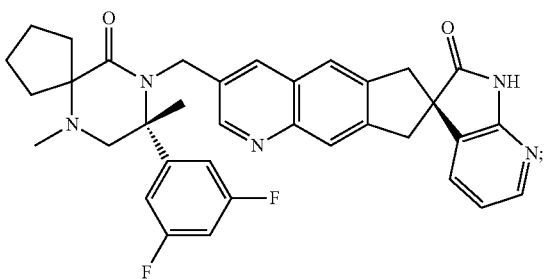

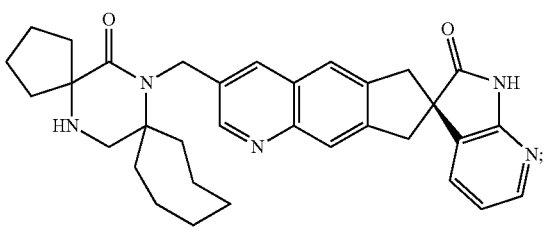

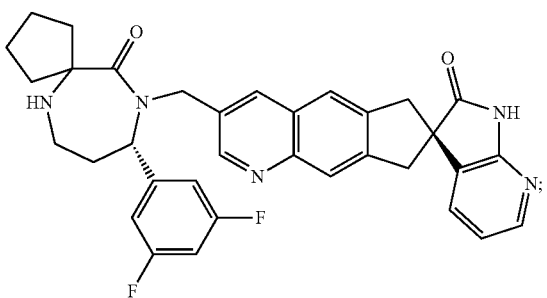

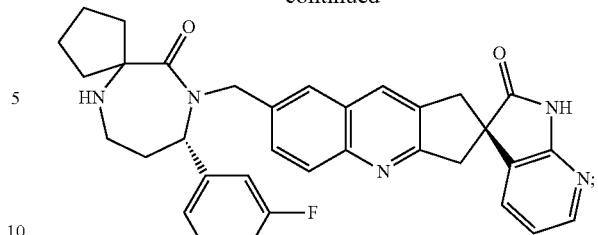

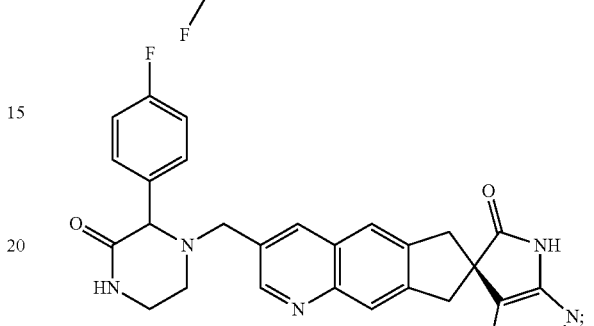

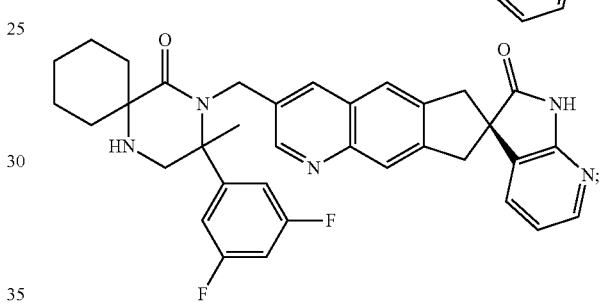

or a pharmaceutically acceptable salt thereof.

19. A pharmaceutical composition which comprises an inert carrier and the compound of claim 1.

20. A method for treating headache in a mammalian patient in need of such which comprises administering to the patient a therapeutically effective amount of the compound of claim 1, or individual stereoisomer thereof.

21. The method of claim 20, wherein headache is migraine headache or cluster headache.

* * * * *

UNITED STATES PATENT AND TRADEMARK OFFICE
CERTIFICATE OF CORRECTION

| | | |
|---|---|---|
| PATENT NO. | : 8,507,477 B2 | Page 1 of 1 |
| APPLICATION NO. | : 13/059164 | |
| DATED | : August 13, 2013 | |
| INVENTOR(S) | : Wood et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 172 days.

Signed and Sealed this
Sixth Day of January, 2015

Michelle K. Lee
*Deputy Director of the United States Patent and Trademark Office*